(12) United States Patent
Kondo et al.

(10) Patent No.: US 11,467,122 B2
(45) Date of Patent: Oct. 11, 2022

(54) GAS SENSOR AND GAS CONCENTRATION MEASUREMENT METHOD

(71) Applicant: NGK INSULATORS, LTD., Aichi (JP)

(72) Inventors: Yuichiro Kondo, Obu (JP); Nobuhiko Mori, Nagoya (JP)

(73) Assignee: NGK INSULATORS, LTD., Nagoya (JP)

( * ) Notice: Subject to any disclaimer, the term of this patent is extended or adjusted under 35 U.S.C. 154(b) by 506 days.

(21) Appl. No.: 16/695,471

(22) Filed: Nov. 26, 2019

(65) Prior Publication Data

US 2020/0166475 A1    May 28, 2020

(30) Foreign Application Priority Data

Nov. 27, 2018 (JP) .............................. JP2018-221537
Nov. 20, 2019 (JP) .............................. JP2019-209534

(51) Int. Cl.
*G01N 27/409* (2006.01)
*F01N 11/00* (2006.01)
*G01N 33/00* (2006.01)

(52) U.S. Cl.
CPC ......... *G01N 27/409* (2013.01); *F01N 11/007* (2013.01); *G01N 33/0054* (2013.01); *F01N 2560/021* (2013.01)

(58) Field of Classification Search
CPC .. G01N 27/409; G01N 33/00; G01N 33/0054; F01N 11/00; F01N 11/007; F01N 2560/021
USPC ....................................................... 73/114.73
See application file for complete search history.

(56) References Cited

U.S. PATENT DOCUMENTS

| 8,904,755 B2* | 12/2014 | Takeda ................ F02N 11/0814 60/284 |
| 2008/0226544 A1* | 9/2008 | Nakamura ............. B01J 8/0411 422/211 |
| 2011/0186431 A1* | 8/2011 | Horisaka ............ G01N 27/4077 156/89.12 |
| 2015/0192084 A1* | 7/2015 | Surnilla ................ F02D 19/087 73/114.73 |
| 2015/0192085 A1* | 7/2015 | Surnilla ................ F02D 19/088 73/114.73 |
| 2016/0032812 A1* | 2/2016 | Lee ........................ F01N 11/007 73/114.73 |

(Continued)

FOREIGN PATENT DOCUMENTS

WO    2017/222002 A1    12/2017

*Primary Examiner* — Peter J Macchiarolo
*Assistant Examiner* — Mohammed E Keramet-Amircolai
(74) *Attorney, Agent, or Firm* — Mattingly & Malur, PC

(57) ABSTRACT

In a gas sensor, which measures a measurement pump current Ip3 of a measurement chamber, while switching a preliminary pump cell of a preliminary chamber ON or OFF at a constant period, there are formed in communication with each other sequentially from a gas introduction port in the interior of a structural body made from a solid electrolyte, a preliminary chamber, an oxygen concentration adjustment chamber, and a measurement chamber. The gas sensor rapidly determines a steady-state value of a measurement pump current Ip3, based on a peak value of a rate of change over time dIp3/dt of the measurement pump current Ip3, thereby hastening an ON/OFF switching period of the preliminary pump cell.

10 Claims, 15 Drawing Sheets

(56) References Cited

U.S. PATENT DOCUMENTS

| | | | |
|---|---|---|---|
| 2018/0074009 A1* | 3/2018 | Okamoto | G01N 27/4074 |
| 2018/0094564 A1* | 4/2018 | Okamoto | G01N 27/4071 |
| 2018/0100828 A1* | 4/2018 | Okamoto | G01N 27/4075 |
| 2019/0128833 A1 | 5/2019 | Nakagaki | |

* cited by examiner

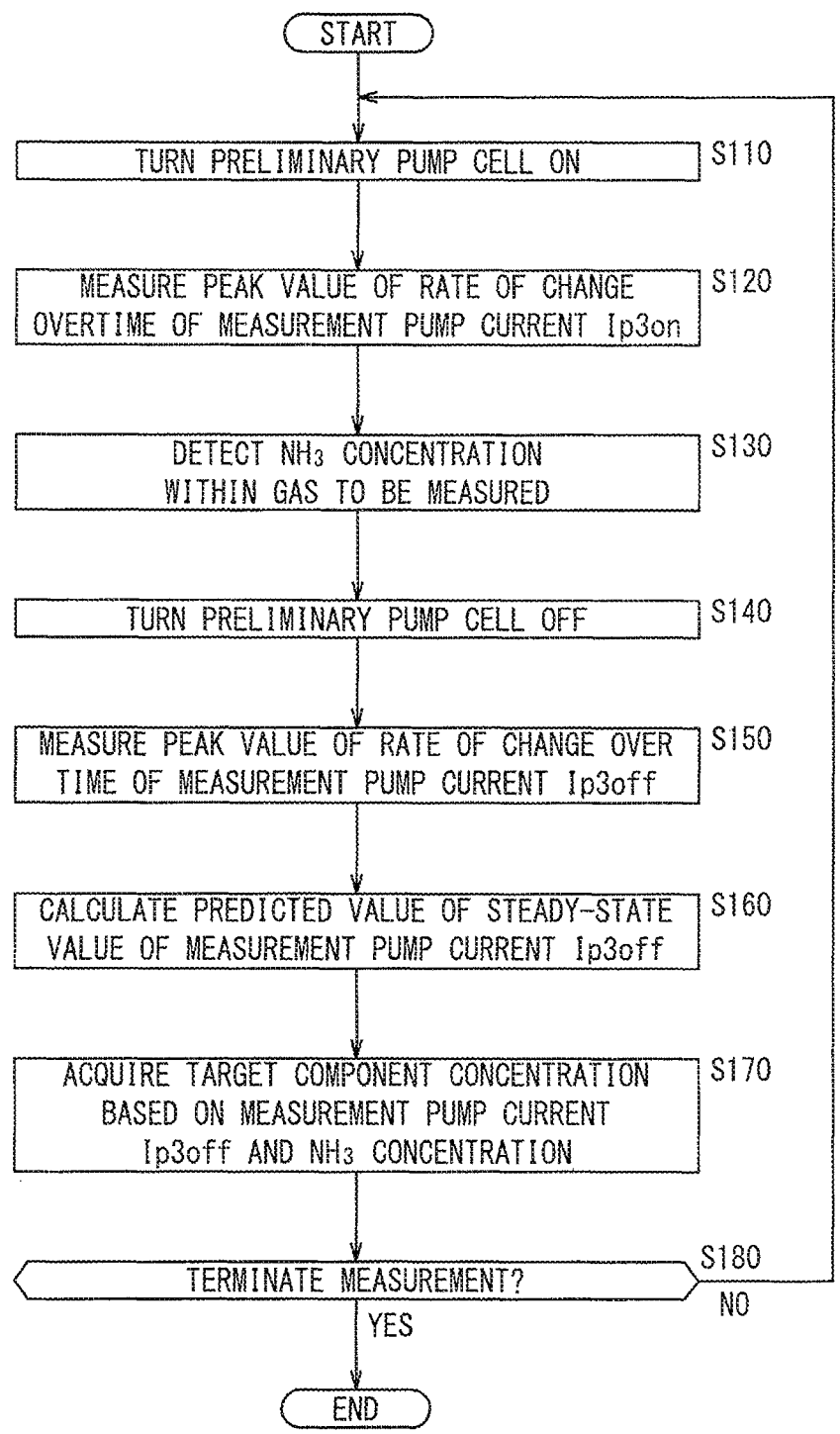

GAS SENSOR AND GAS CONCENTRATION MEASUREMENT METHOD

CROSS-REFERENCE TO RELATED APPLICATION

This application is based upon and claims the benefit of priority from Japanese Patent Applications No. 2018-221537 filed on Nov. 27, 2018 and No. 2019-209534 filed on Nov. 20, 2019, the contents of which are incorporated herein by reference.

BACKGROUND OF THE INVENTION

Field of the Invention

The present invention relates to a gas sensor and a gas concentration measurement method in which an oxygen ion conductive solid electrolyte is used.

Description of the Related Art

Conventionally, gas sensors have been proposed which measure concentrations of a plurality of target components such as nitrogen oxide (NO) and ammonia ($NH_3$) and the like that coexist in the presence of oxygen, such as in an exhaust gas.

For example, in International Publication No. WO 2017/222002, a gas sensor is disclosed in which, in an oxygen ion conductive solid electrolyte, a preliminary chamber, a main chamber, an auxiliary chamber, and a measurement chamber which are partitioned by diffusion resistance members are provided, together with pumping electrodes being disposed in each of the respective chambers. With such a gas sensor, the progression or stoppage of an oxidation reaction of $NH_3$ into NO taking place inside the preliminary chamber is switched by switching between driving (ON) or stopping (OFF) of a preliminary pump cell of the preliminary chamber. In addition, the gas concentrations of $NH_3$ and NO are measured on the basis of a change in a pumping current (referred to hereinafter as a measurement pump current Ip3) of a measurement electrode inside the measurement chamber, which occurs due to a difference in the diffusion rate of $NH_3$ and NO from the preliminary chamber into the main chamber.

SUMMARY OF THE INVENTION

In the gas sensor described in International Publication No. WO 2017/222002, the measurement pump current Ip3 is acquired while switching is carried out at regular intervals between ON or OFF of the preliminary pump cell of the preliminary chamber. When the preliminary pump cell is switched between ON or OFF, the measurement pump current Ip3 changes in a transient manner and thereafter settles to a steady-state value. Accordingly, in order to acquire the measurement pump current Ip3, it is necessary to wait a certain time period until the measurement pump current Ip3 settles to a steady-state value, and a switching period of the operative state of the preliminary pump cell is set to be longer than the time period until the measurement pump current Ip3 settles to a steady-state value.

However, the state of the inflowing exhaust gas changes moment by moment. Therefore, when the concentration of the measurement target gas varies during the switching period, the steady-state value of the measurement pump current Ip3 also changes. As a result, cases occur in which the concentration of the target component gas that is reflected by the measurement pump current Ip3on when the preliminary pump cell is turned ON differs from the concentration of the target component gas that is reflected by the measurement pump current Ip3off when the preliminary pump cell is turned OFF. In this manner, if the concentration of the target component in the measurement chamber significantly fluctuates during the switching period of one cycle of the preliminary pump cell, a problem results in that the preconditions for measurement are not satisfied, and the measurement accuracy is lowered.

The present invention has the object of providing a gas sensor and a gas concentration measurement method, which are capable of preventing a decrease in measurement accuracy due to a delay in the measurement time of the measurement pump current Ip3.

One aspect of the present invention is characterized by a gas sensor configured to measure concentrations of a plurality of components existing in presence of oxygen, comprising a structural body made up from a solid electrolyte that exhibits oxygen ion conductivity, a gas introduction port formed in the structural body and into which a gas to be measured is introduced, a preliminary chamber including a preliminary pump electrode and communicating with the gas introduction port, an oxygen concentration adjustment chamber including a pump electrode and communicating with the preliminary chamber, a measurement chamber including a measurement electrode and communicating with the oxygen concentration adjustment chamber, a preliminary oxygen concentration control unit configured to control an oxygen concentration inside the preliminary chamber based on a voltage of the preliminary pump electrode, a specified component measurement unit configured to detect a measurement pump current (Ip3) flowing through an exterior side pump electrode and the measurement electrode, under an operation of the preliminary oxygen concentration control unit, and a target component acquisition unit configured to acquire a concentration of a target component within the gas to be measured, on a basis of an amount of change ($\Delta Ip3$) between a measurement pump current (Ip3on) from the specified component measurement unit at a time of a first operation of the preliminary oxygen concentration control unit and a measurement pump current (Ip3off) from the specified component measurement unit at a time of a second operation of the preliminary oxygen concentration control unit, and one of the measurement pump current (Ip3on) and the measurement pump current (Ip3off), wherein the specified component measurement unit is configured to determine a steady-state value of the measurement pump current (Ip3on) or a steady-state value of the measurement pump current (Ip3off), based on a peak value of a rate of change over time of the measurement pump current (Ip3) when an operation of the preliminary oxygen concentration control unit is switched between the first operation and the second operation.

Another aspect of the present invention is characterized by a gas concentration measurement method in which a gas sensor is used, the gas sensor comprising a structural body made up from a solid electrolyte that exhibits oxygen ion conductivity, a gas introduction port formed in the structural body and into which a gas to be measured is introduced, a preliminary chamber including a preliminary pump electrode and communicating with the gas introduction port, an oxygen concentration adjustment chamber including a pump electrode and communicating with the preliminary chamber, a measurement chamber including a measurement electrode and communicating with the oxygen concentration adjustment chamber, a preliminary oxygen concentration control unit configured to control an oxygen concentration inside the preliminary chamber based on a voltage of the preliminary pump electrode, a specified component measurement unit configured to detect a measurement pump current (Ip3) flowing through an exterior side pump electrode and the measurement electrode under an operation of the preliminary oxygen concentration control unit, and a target component acquisition unit configured to acquire a concentration of a target component within the gas to be measured, on a basis of an amount of change (ΔIp3) between a measurement pump current (Ip3on) from the specified component measurement unit at a time of a first operation of the preliminary oxygen concentration control unit and a measurement pump current (Ip3off) from the specified component measurement unit at a time of a second operation of the preliminary oxygen concentration control unit, and one of the measurement pump current (Ip3on) and the measurement pump current (Ip3off), the gas concentration measurement method comprising an operation switching step of performing a control to switch between the first operation and the second operation of the preliminary oxygen concentration control unit, a determining step of, by the specified component measurement unit, determining a peak value of a rate of change over time of the measurement pump current (Ip3) accompanying the control to switch between the first operation and the second operation of the preliminary oxygen concentration control unit, a determining step of, by the specified component measurement unit, determining a steady-state value of the measurement pump current (Ip3), from a previously determined correlation between the peak value of the rate of change over time of the measurement pump current (Ip3) and the steady-state value of the measurement pump current (Ip3), and an acquisition step of, by the target component acquisition unit, acquiring the concentration of the target component within the gas to be measured, based on the steady-state value of the measurement pump current (Ip3) from the specified component measurement unit.

In accordance with the gas sensor and the gas concentration measurement method of the above-described aspects, by focusing attention on the rate of change over time of the pump current value (measurement pump current) of the measurement electrode accompanying switching of the operative state of the preliminary pump cell in the preliminary chamber, the predicted value of the steady-state value of the pump current value of the measurement electrode is determined. Consequently, the steady-state value of the pump current value can be determined before the pump current value of the measurement electrode has settled to a steady state. Therefore, switching of the operative state of the preliminary pump cell can be carried out before the pump current value of the measurement electrode has settled to a steady-state value, and the switching period of the operative state of the preliminary pump cell can be shortened. As a result, a delay in the measurement time of the measurement pump current Ip3 can be reduced, and a decrease in measurement accuracy can be prevented.

The above and other objects, features, and advantages of the present invention will become more apparent from the following description when taken in conjunction with the accompanying drawings, in which preferred embodiments of the present invention are shown by way of illustrative example.

BRIEF DESCRIPTION OF THE DRAWINGS

FIG. 6 is a diagram schematically showing a change and a rate of change over time in the measurement pump current Ip3 when the preliminary pump cell is switched from OFF to ON;

FIG. 15 is a flowchart showing a process of acquiring the measurement pump current Ip3 according to a second embodiment.

DESCRIPTION OF THE PREFERRED EMBODIMENTS

Exemplary embodiments of a gas sensor and a gas concentration measurement method according to the present invention will be presented and described below with reference to FIGS. 1 to 15. In the present specification, the term "to" when used to indicate a numerical range is used with the implication of including the numerical values written before or after the term as a lower limit value or an upper limit value of the numerical range.

First Embodiment

Figure 1:
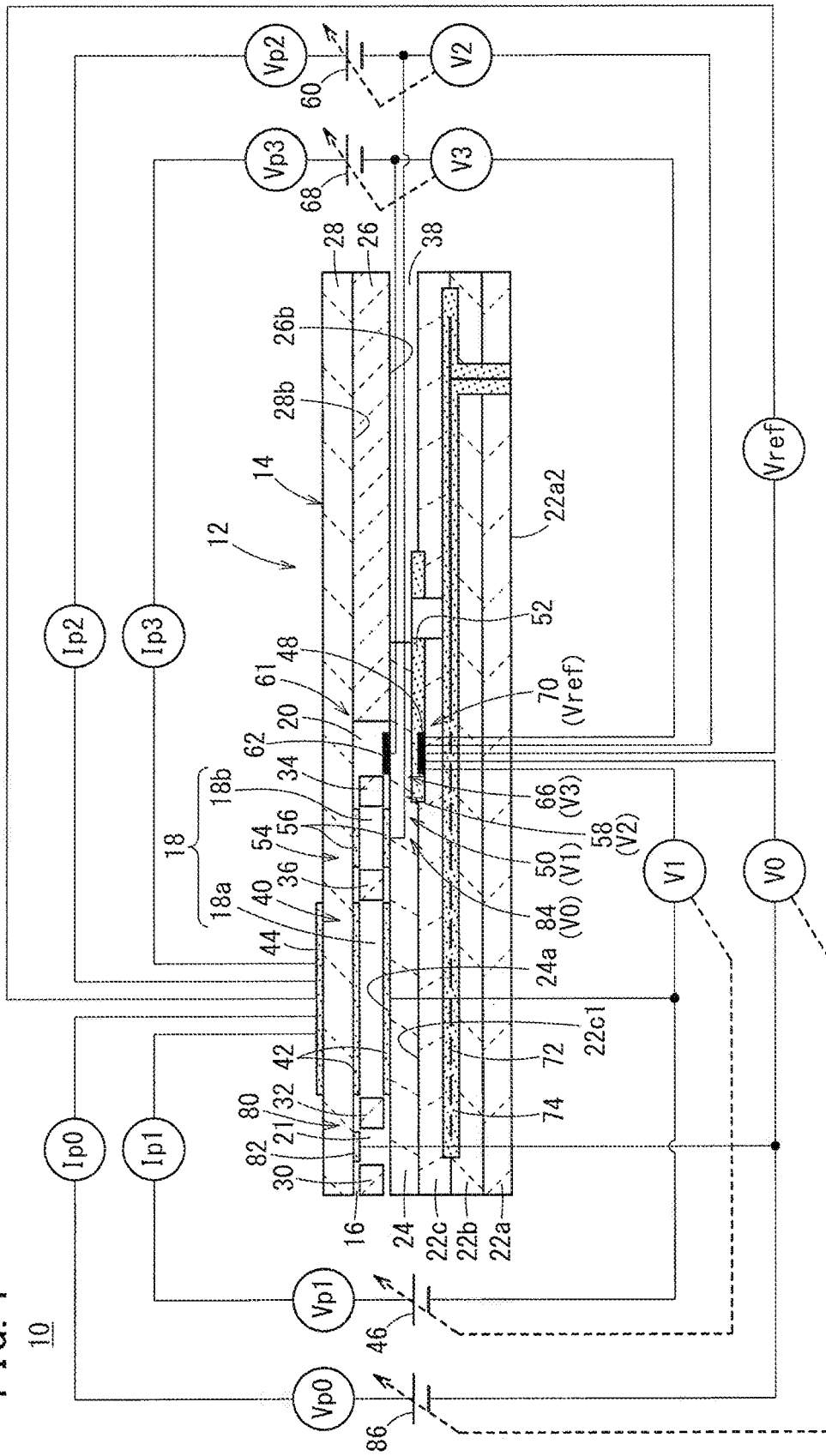
FIG. 1 is a cross-sectional view in which there is shown one structural example of a gas sensor according to a first embodiment.
Figure 2:
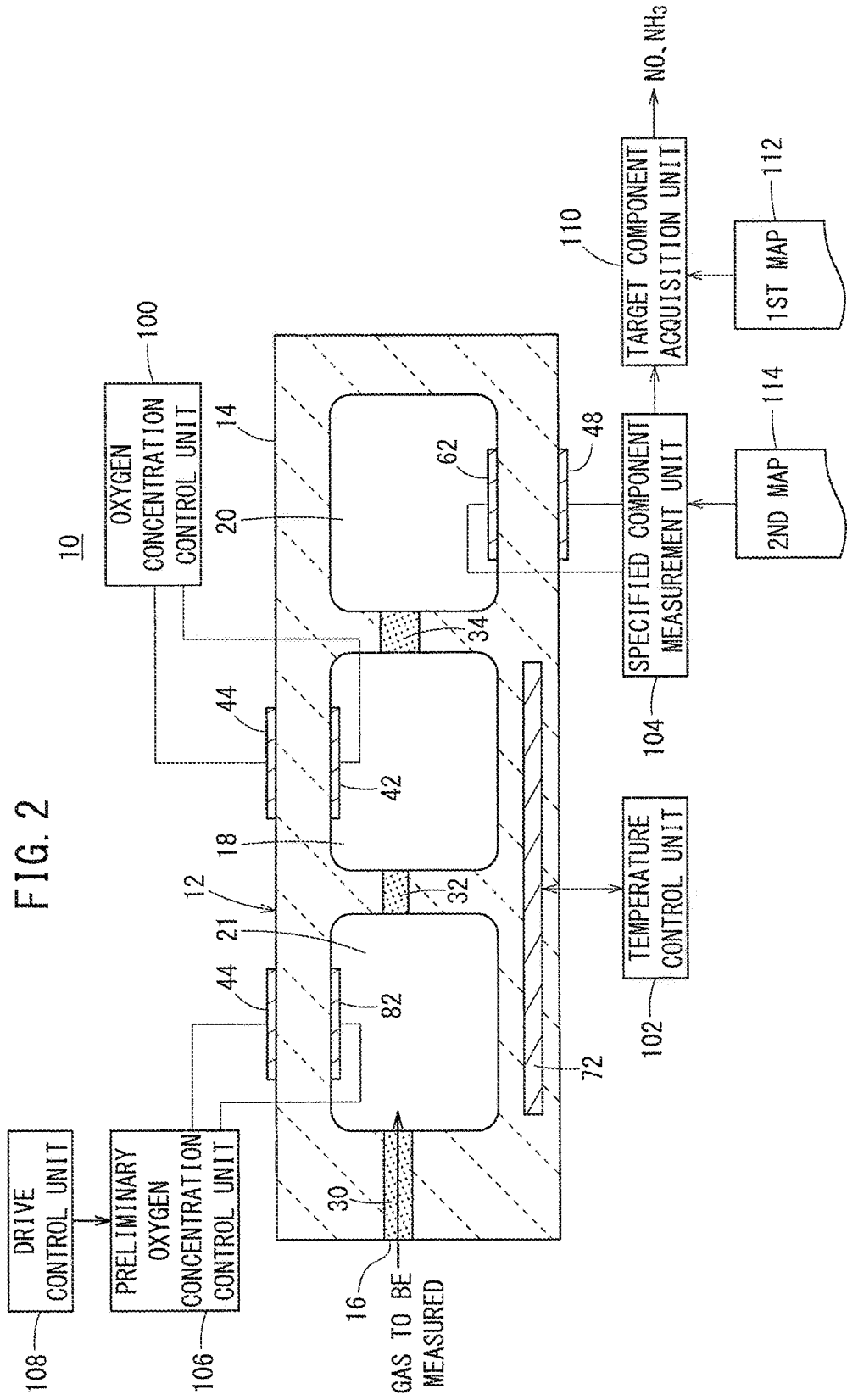
FIG. 2 is a block diagram of the gas sensor shown in FIG. 1.

As shown in FIGS. 1 and 2, a gas sensor 10 according to the present embodiment includes a sensor element 12. The sensor element 12 includes a structural body 14 made up from a solid electrolyte that exhibits at least oxygen ion conductivity, a gas introduction port 16 formed in the structural body 14 and into which a gas to be measured is introduced, an oxygen concentration adjustment chamber 18 formed in the structural body 14 and communicating with the gas introduction port 16, and a measurement chamber 20 formed in the structural body 14 and communicating with the oxygen concentration adjustment chamber 18.

The oxygen concentration adjustment chamber 18 includes a main chamber 18a disposed on the side of the gas introduction port 16, and an auxiliary chamber 18b communicating with the main chamber 18a. The measurement chamber 20 communicates with the auxiliary chamber 18b. The oxygen concentration adjustment chamber 18 may be constituted by the main chamber 18a only.

Furthermore, the gas sensor 10 includes a preliminary chamber 21 provided between the gas introduction port 16 and the main chamber 18a within the structural body 14. The main chamber 18a communicates with the gas introduction port 16 via the preliminary chamber 21.

The structural body 14 having such a plurality of chambers 18a, 18b, 20, and 21 is constituted by stacking a plurality of layers of substrates made from ceramics, for example. More specifically, the structural body 14 of the sensor element 12 is constituted by six layers made up from a first substrate 22a, a second substrate 22b, a third substrate 22c, a first solid electrolyte layer 24, a spacer layer 26, and a second solid electrolyte layer 28, which are stacked in this order from below. The respective layers are constituted, for example, from an oxygen ion conductive solid electrolyte such as zirconia ($ZrO_2$) or the like.

The gas introduction port 16 is provided at one end of the sensor element 12. The gas introduction port 16 is formed between a lower surface 28b of the second solid electrolyte layer 28 and an upper surface 24a of the first solid electrolyte layer 24.

Furthermore, between the lower surface 28b of the second solid electrolyte layer 28 and the upper surface 24a of the first solid electrolyte layer 24, there are formed a first diffusion rate control member 30, the preliminary chamber 21, a second diffusion rate control member 32, the oxygen concentration adjustment chamber 18, a third diffusion rate control member 34, and the measurement chamber 20. A fourth diffusion rate control member 36 is provided between the main chamber 18a and the auxiliary chamber 18b that make up the oxygen concentration adjustment chamber 18.

The gas introduction port 16, the first diffusion rate control member 30, the preliminary chamber 21, the second diffusion rate control member 32, the main chamber 18a, the fourth diffusion rate control member 36, the auxiliary chamber 18b, the third diffusion rate control member 34, and the measurement chamber 20 are formed adjacent to each other in a manner communicating in this order. The portion from the gas introduction port 16 leading to the measurement chamber 20 is also referred to as a gas flow section.

The gas introduction port 16, the preliminary chamber 21, the main chamber 18a, the auxiliary chamber 18b, and the measurement chamber 20 are formed so as to penetrate through the spacer layer 26 in the thickness direction. The lower surface 28b of the second solid electrolyte layer 28 is exposed on upper parts of these chambers 18a, 18b, 20, and 21, and the upper surface 24a of the first solid electrolyte layer 24 is exposed on lower parts thereof. Further, side parts of the chambers 18a, 18b, 20, and 21 are partitioned by the spacer layer 26 or the diffusion rate control members 30, 32, 34, and 36.

Any one of the first diffusion rate control member 30, the third diffusion rate control member 34, and the fourth diffusion rate control member 36 is provided with two horizontally elongated slits. More specifically, the slits include in upper and lower portions thereof slit-shaped openings which are elongated in a direction perpendicular to the surface of the drawing sheet. Further, the second diffusion rate control member 32 is provided with a single horizontally elongated slit.

Further, a reference gas introduction space 38 is provided at the other end (an end opposite to the end where the gas introduction port 16 is provided) of the sensor element 12. The reference gas introduction space 38 is formed between an upper surface 22c1 of the third substrate 22c and a lower surface 26b of the spacer layer 26. Further, a side portion of the reference gas introduction space 38 is partitioned by a side surface of the first solid electrolyte layer 24. For example, oxygen or atmospheric air is introduced as a reference gas into the reference gas introduction space 38.

The gas introduction port 16 is a location that opens to the external space, and the target gas to be measured is drawn into the sensor element 12 from the external space through the gas introduction port 16.

The first diffusion rate control member 30 is a location that imparts a predetermined diffusion resistance to the gas to be measured which is introduced from the gas introduction port 16 into the preliminary chamber 21. Details concerning the preliminary chamber 21 will be described later.

The second diffusion rate control member 32 is a location that imparts a predetermined diffusion resistance to the gas to be measured which is introduced from the preliminary chamber 21 into the main chamber 18a.

The main chamber 18a is provided as a space for the purpose of adjusting an oxygen partial pressure within the gas to be measured that is introduced from the gas introduction port 16. The oxygen partial pressure is adjusted by operation of a main pump cell 40.

The main pump cell 40 comprises an electrochemical pump cell, also referred to as a main electrochemical pumping cell, which is constituted by a main pump electrode 42, an exterior side pump electrode 44, and an oxygen ion conductive solid electrolyte which is sandwiched between the two pump electrodes. The main pump electrode 42 is provided substantially over the entire surfaces, respectively, of the upper surface 24a of the first solid electrolyte layer 24, the lower surface 28b of the second solid electrolyte layer 28, and side surfaces of the spacer layer 26 that define the main chamber 18a. The exterior side pump electrode 44 is formed on the upper surface of the second solid electrolyte layer 28. The position of the exterior side pump electrode 44 is preferably disposed in a region corresponding to the main pump electrode 42 in a manner of being exposed to the external space. The main pump electrode 42 is preferably made of a material having a weakened reduction capability with respect to the nitrogen oxide (NO) component within the gas to be measured. For example, the main pump electrode can be configured as a rectangular porous cermet electrode as viewed in plan.

The main pump cell 40 applies a first pump voltage Vp1 supplied from a first variable power source 46 which is provided externally of the sensor element 12, and by allowing a first pump current Ip1 to flow between the exterior side pump electrode 44 and the main pump electrode 42, it is possible to pump oxygen in the interior of the main chamber 18a out to the exterior, or alternatively, to pump oxygen in the external space into the main chamber 18a.

Further, the sensor element 12 includes a first oxygen partial pressure detecting sensor cell 50 which is an electrochemical sensor cell. The first oxygen partial pressure detecting sensor cell 50 includes the main pump electrode 42, a reference electrode 48, and the oxygen ion conductive first solid electrolyte layer 24 sandwiched between these electrodes. The reference electrode 48 is an electrode formed between the first solid electrolyte layer 24 and the third substrate 22c, and is made of the same porous cermet as the exterior side pump electrode 44. The reference electrode 48 is formed with a rectangular shape as viewed in plan. Further, around the periphery of the reference electrode 48, a reference gas introduction layer 52 is provided, which is made from porous alumina and is connected to the reference gas introduction space 38. The reference gas in the reference gas introduction space 38 is introduced to the surface of the reference electrode 48 via the reference gas introduction layer 52. The first oxygen partial pressure detecting sensor cell 50 generates a first electromotive force V1 between the main pump electrode 42 and the reference electrode 48, which is caused by the difference in oxygen concentration between the atmosphere inside the main chamber 18a and the reference gas in the reference gas introduction space 38.

The first electromotive force V1 generated in the first oxygen partial pressure detecting sensor cell 50 changes depending on the oxygen partial pressure of the atmosphere existing in the main chamber 18a. In accordance with the aforementioned first electromotive force V1, the sensor element 12 feedback-controls the first variable power source 46 of the main pump cell 40. Consequently, the first pump voltage Vp1, which is applied by the first variable power source 46 to the main pump cell 40, can be controlled in accordance with the oxygen partial pressure of the atmosphere in the main chamber 18a.

The fourth diffusion rate control member 36 imparts a predetermined diffusion resistance to the gas to be measured, the oxygen concentration (oxygen partial pressure) of which is controlled by operation of the main pump cell 40 in the main chamber 18a, and is a location that guides the gas to be measured into the auxiliary chamber 18b.

The auxiliary chamber 18b is provided as a space for further carrying out adjustment of the oxygen partial pressure by an auxiliary pump cell 54, with respect to the gas to be measured which is introduced through the fourth diffusion rate control member 36, after the oxygen concentration (oxygen partial pressure) has been adjusted beforehand in the main chamber 18a. In accordance with this feature, the oxygen concentration inside the auxiliary chamber 18b can be kept constant highly accurately, and it is possible to measure the NOx concentration with high accuracy.

The auxiliary pump cell 54 is an electrochemical pump cell, and is constituted by an auxiliary pump electrode 56, which is provided substantially over the entire area that faces toward the auxiliary chamber 18b in the lower surface 28b of the second solid electrolyte layer 28, the exterior side pump electrode 44, and the second solid electrolyte layer 28. Moreover, in the same manner as the main pump electrode 42, the auxiliary pump electrode 56 is also formed using a material having a weakened reduction capability with respect to the NOx component within the gas to be measured.

The auxiliary pump cell 54, by applying a desired second pump voltage Vp2 between the auxiliary pump electrode 56 and the exterior side pump electrode 44, is capable of pumping out oxygen within the atmosphere inside the auxiliary chamber 18b into the external space, or alternatively, is capable of pumping in oxygen from the external space into the auxiliary chamber 18b.

Further, in order to control the oxygen partial pressure within the atmosphere inside the auxiliary chamber 18b, an electrochemical sensor cell is constituted by the auxiliary pump electrode 56, the reference electrode 48, the second solid electrolyte layer 28, the spacer layer 26, and the first solid electrolyte layer 24. More specifically, a second oxygen partial pressure detecting sensor cell 58 is constituted thereby for controlling the auxiliary pump.

The second oxygen partial pressure detecting sensor cell 58 generates a second electromotive force V2 between the auxiliary pump electrode 56 and the reference electrode 48, which is caused by a difference in the oxygen concentration between the atmosphere inside the auxiliary chamber 18b and the reference gas in the reference gas introduction space 38. The second electromotive force V2 generated in the second oxygen partial pressure detecting sensor cell 58 changes depending on the oxygen partial pressure of the atmosphere existing in the auxiliary chamber 18b.

Based on the aforementioned second electromotive force V2, the sensor element 12 carries out pumping of the auxiliary pump cell 54 by controlling a second variable power source 60. Consequently, the oxygen partial pressure within the atmosphere inside the auxiliary chamber 18b is controlled so as to become a low partial pressure that does not substantially influence the measurement of NOx.

Further, together therewith, a second pump current Ip2 of the auxiliary pump cell 54 is used so as to control the second electromotive force V2 of the second oxygen partial pressure detecting sensor cell 58. More specifically, the second pump current Ip2 is input as a control signal to the second oxygen partial pressure detecting sensor cell 58. As a result, the second electromotive force V2 is controlled, and the gradient of the oxygen partial pressure within the gas to be measured, which is introduced into the auxiliary chamber 18b through the fourth diffusion rate control member 36, is controlled to remain constant at all times. When the gas sensor 10 is used as a NOx sensor, by the effects of the main pump cell 40 and the auxiliary pump cell 54, the oxygen concentration inside the auxiliary chamber 18b is maintained at a predetermined value with high accuracy for each of the respective conditions.

The third diffusion rate control member 34 imparts a predetermined diffusion resistance to the gas to be measured, the oxygen concentration (oxygen partial pressure) of which is controlled by operation of the auxiliary pump cell 54 in the auxiliary chamber 18b, and is a location that guides the gas to be measured into the measurement chamber 20.

Measurement of the NOx concentration is primarily performed by operation of a measurement pump cell 61 provided in the measurement chamber 20. The measurement pump cell 61 is an electrochemical pump cell constituted by a measurement electrode 62, the exterior side pump electrode 44, the second solid electrolyte layer 28, the spacer layer 26, and the first solid electrolyte layer 24. The measurement electrode 62 is provided, for example, on the upper surface 24a of the first solid electrolyte layer 24 inside the measurement chamber 20, and is constituted by a material having a strengthened reduction capability with respect to the NOx component within the gas to be measured to be higher than that of the main pump electrode 42. The measurement electrode 62 can be, for example, a porous cermet electrode. Further, a material preferably is used for the measurement electrode 62 that also functions as a NOx reduction catalyst for reducing NOx that exists within the atmosphere.

The measurement pump cell 61 generates oxygen by decomposing nitrogen oxide around the periphery of the measurement electrode 62 inside the measurement chamber 20. Furthermore, the measurement pump cell 61 is capable of pumping out the oxygen generated at the measurement electrode 62, and detecting the generated amount of oxygen as a measurement pump current Ip3, or stated otherwise, as a sensor output.

Further, in order to detect the oxygen partial pressure around the periphery of the measurement electrode 62 inside the measurement chamber 20, an electrochemical sensor cell, and more specifically, a third oxygen partial pressure detecting sensor cell 66 for controlling the measurement pump, is constituted by the first solid electrolyte layer 24, the measurement electrode 62, and the reference electrode 48. A third variable power source 68 is controlled based on a third electromotive force V3 detected by the third oxygen partial pressure detecting sensor cell 66.

The gas to be measured, which is introduced into the auxiliary chamber 18*b*, reaches the measurement electrode 62 inside the measurement chamber 20 through the third diffusion rate control member 34, under a condition in which the oxygen partial pressure is controlled. Nitrogen oxide existing within the gas to be measured around the periphery of the measurement electrode 62 is reduced to thereby generate oxygen. In this instance, the generated oxygen is subjected to pumping by the measurement pump cell 61. At this time, a third pump voltage Vp3 of the third variable power source 68 is controlled in a manner so that the third electromotive force V3 detected by the third oxygen partial pressure detecting sensor cell 66 becomes constant. The amount of oxygen generated around the periphery of the measurement electrode 62 is proportional to the nitrogen oxide concentration within the gas to be measured. Accordingly, the nitrogen oxide concentration within the gas to be measured can be calculated using the measurement pump current Ip3 of the measurement pump cell 61. More specifically, the measurement pump cell 61 constitutes a specified component measurement unit 104 that measures the concentration of a specified component (NO) inside the measurement chamber 20.

Further, the gas sensor 10 includes an electrochemical sensor cell 70. The sensor cell 70 is constituted by the second solid electrolyte layer 28, the spacer layer 26, the first solid electrolyte layer 24, the third substrate 22*c*, the exterior side pump electrode 44, and the reference electrode 48. In accordance with the electromotive force Vref obtained by the sensor cell 70, it is possible to detect the oxygen partial pressure within the gas to be measured existing externally of the sensor.

Furthermore, in the sensor element 12, a heater 72 is formed in a manner of being sandwiched from above and below between the second substrate 22*b* and the third substrate 22*c*. The heater 72 generates heat by being supplied with power from the exterior through a non-illustrated heater electrode provided on a lower surface 22*a*2 of the first substrate 22*a*. As a result of the heat generated by the heater 72, the oxygen ion conductivity of the solid electrolyte that constitutes the sensor element 12 is enhanced. The heater 72 is embedded over the entire region of the preliminary chamber 21, the oxygen concentration adjustment chamber 18, and the measurement chamber 20, and a predetermined location of the sensor element 12 can be heated and maintained at a predetermined temperature. Moreover, a heater insulating layer 74 made of alumina or the like is formed above and below the heater 72, for the purpose of obtaining electrical insulation thereof from the second substrate 22*b* and the third substrate 22*c*. Hereinafter, the heater 72, the heater electrode, and the heater insulating layer 74 may also be referred to collectively as a heater portion.

In addition, the preliminary chamber 21 is driven by a later-described drive control unit 108 (see FIG. 2), and during driving thereof, functions as a space for adjusting the oxygen partial pressure within the gas to be measured which is introduced from the gas introduction port 16. The oxygen partial pressure is adjusted by operation of a preliminary pump cell 80.

The preliminary pump cell 80 is an electrochemical pump cell, which is constituted by a preliminary pump electrode 82 provided substantially over the entire area that faces toward the preliminary chamber 21 in the lower surface 28*b* of the second solid electrolyte layer 28, the exterior side pump electrode 44, and the second solid electrolyte layer 28.

Moreover, in the same manner as the main pump electrode 42, the preliminary pump electrode 82 is also formed using a material having a weakened reduction capability with respect to the NOx component within the gas to be measured.

The preliminary pump cell 80, by applying a desired preliminary voltage Vp0 between the preliminary pump electrode 82 and the exterior side pump electrode 44, is capable of pumping out oxygen within the atmosphere inside the preliminary chamber 21 into the external space, or alternatively, is capable of pumping in oxygen from the external space into the preliminary chamber 21.

Further, the gas sensor 10 includes a preliminary oxygen partial pressure detecting sensor cell 84 for controlling the preliminary pump, in order to control the oxygen partial pressure within the atmosphere inside the preliminary chamber 21. The preliminary oxygen partial pressure detecting sensor cell 84 includes the preliminary pump electrode 82, the reference electrode 48, the second solid electrolyte layer 28, the spacer layer 26, and the first solid electrolyte layer 24. The preliminary oxygen partial pressure detecting sensor cell 84 detects as a preliminary electromotive force V0 the electromotive force between the preliminary pump electrode 82 and the reference electrode 48, which is generated by a difference between the oxygen concentration within the atmosphere inside the preliminary chamber 21 and the oxygen concentration within the reference gas.

Moreover, the preliminary pump cell 80 carries out pumping by a preliminary variable power source 86, the voltage of which is controlled based on a preliminary electromotive force V0 detected by the preliminary oxygen partial pressure detecting sensor cell 84. Consequently, the oxygen partial pressure within the atmosphere inside the preliminary chamber 21 is controlled so as to become a low partial pressure that does not substantially influence the measurement of NOx.

Further, together therewith, a preliminary pump current Ip0 thereof is used so as to control the preliminary electromotive force V0 of the preliminary oxygen partial pressure detecting sensor cell 84. More specifically, the preliminary pump current Ip0 is input as a control signal to the preliminary oxygen partial pressure detecting sensor cell 84, and by controlling the preliminary electromotive force V0, the gradient of the oxygen partial pressure within the gas to be measured, which is introduced from the first diffusion rate control member 30 into the preliminary chamber 21, is controlled so as to remain constant at all times.

The preliminary chamber 21 also functions as a buffer space. More specifically, it is possible to cancel fluctuations in the concentration of the gas to be measured, which occur due to pressure fluctuations of the gas to be measured in the external space. As such pressure fluctuations of the gas to be measured, there may be cited, for example, pulsations in the exhaust pressure of an automotive exhaust gas.

Furthermore, as shown schematically in FIG. 2, the gas sensor 10 includes an oxygen concentration control unit 100 (main oxygen concentration control unit) that controls the oxygen concentration inside the oxygen concentration adjustment chamber 18, a temperature control unit 102 that controls the temperature of the sensor element 12, the specified component measurement unit 104 that measures the concentration of a specified component (NO or $NH_3$) inside the measurement chamber 20, a preliminary oxygen concentration control unit 106, the drive control unit 108, and a target component acquisition unit 110.

Moreover, the oxygen concentration control unit 100, the temperature control unit 102, the specified component measurement unit 104, the preliminary oxygen concentration control unit 106, the drive control unit 108, and the target component acquisition unit 110 are constituted by one or more electronic circuits having, for example, one or a plurality of CPUs (central processing units), memory devices, and the like. The electronic circuits are software-based functional units in which predetermined functions are realized, for example, by the CPUs executing programs stored in the storage device. Of course, the electronic circuits may be constituted by an integrated circuit such as an FPGA (Field-Programmable Gate Array), in which the plurality of electronic circuits are connected according to the functions thereof.

By being equipped with the preliminary chamber 21, the preliminary oxygen concentration control unit 106, the drive control unit 108, and the target component acquisition unit 110, in addition to the above-described oxygen concentration adjustment chamber 18, the oxygen concentration control unit 100, the temperature control unit 102, and the specified component measurement unit 104, the gas sensor 10 is made capable of acquiring the respective concentrations of NO (nitric oxide) and $NH_3$ (ammonia).

On the basis of the preset oxygen concentration condition, and the first electromotive force V1 generated in the first oxygen partial pressure detecting sensor cell 50 (see FIG. 1), the oxygen concentration control unit 100 feedback-controls the first variable power source 46, and adjusts the oxygen concentration inside the oxygen concentration adjustment chamber 18 to a concentration in accordance with the above-described condition.

The temperature control unit 102 feedback-controls the heater 72 on the basis of a preset sensor temperature condition, and the measured value from a temperature sensor (not shown) that measures the temperature of the sensor element 12, whereby the temperature of the sensor element 12 is adjusted to a temperature in accordance with the above-described condition.

By the oxygen concentration control unit 100 and the temperature control unit 102, the gas sensor 10 controls the state inside the oxygen concentration adjustment chamber 18, so as to convert all of the $NH_3$ into NO, without causing decomposition of NO inside the oxygen concentration adjustment chamber 18.

The specified component measurement unit 104 detects and outputs the measurement pump current Ip3 flowing between the measurement electrode 62 and the exterior side pump electrode 44. Further, after switching of the preliminary pump cell 80 has been carried out, the specified component measurement unit 104 determines a rate of change over time dIp3/dt of the measurement pump current Ip3, and detects the peak value thereof. Furthermore, the specified component measurement unit 104 refers to a second map 114, and determines an amount of change $\Delta Ip3$ from the peak value of the rate of change over time dIp3/dt of the measurement pump current Ip3 until the steady-state value of the measurement pump current Ip3 is reached, and by adding the amount of change $\Delta Ip3$ to the measurement pump current Ip3 prior to switching, obtains a steady-state value (predicted value) of the measurement pump current Ip3. Moreover, the second map 114 includes a data group in which there is registered a relationship with the amount of change $\Delta Ip3$ until the steady-state value of the measurement pump current Ip3 is reached, for each of points specified by peak values of the rate of change over time dIp3/dt of the measurement pump current Ip3 accompanying switching operations of the preliminary pump cell 80 between ON and OFF. In addition, the second map 114 may further be provided with a data group in which there is registered a relationship with the $NH_3$ concentration within the gas to be measured, for each of respective points specified by the peak values of the rate of change over time dIp3/dt of the measurement pump current Ip3 accompanying switching operations of the preliminary pump cell 80 between ON and OFF. Concerning the data groups that are registered in the second map 114, information (relationship) is used that is obtained in advance through experiment or simulation.

On the basis of the preset oxygen concentration condition, and the preliminary electromotive force V0 generated in the preliminary oxygen partial pressure detecting sensor cell 84 (see FIG. 1), the preliminary oxygen concentration control unit 106 feedback-controls the preliminary variable power source 86, thereby adjusting the oxygen concentration inside the preliminary chamber 21 to a concentration in accordance with the condition.

In addition, the target component acquisition unit 110 acquires the respective concentrations of NO and $NH_3$ on the basis of a difference between the sensor output from the specified component measurement unit 104 in accordance with a first operation of the preliminary oxygen concentration control unit 106, and the sensor output from the specified component measurement unit 104 in accordance with a second operation of the preliminary oxygen concentration control unit 106.

In this instance, the NO and the $NH_3$ within the gas to be measured are changed in the following manner, in accordance with a preliminary voltage Vp0 applied to the preliminary pump electrode 82 by the preliminary oxygen concentration control unit 106.

First, in a first voltage range, the $NH_3$ inside the preliminary chamber 21 is maintained in the form of $NH_3$. The $NH_3$ inside the preliminary chamber 21, while remaining in the form of $NH_3$, passes through the second diffusion rate control member 32 and arrives at the interior of the oxygen concentration adjustment chamber 18. Further, the NO inside the preliminary chamber 21, while remaining in the form of NO, passes through the second diffusion rate control member 32 and arrives at the interior of the oxygen concentration adjustment chamber 18.

In a second voltage range, the $NH_3$ inside the preliminary chamber 21 is oxidized into NO, passes through the second diffusion rate control member 32 and arrives at the oxygen concentration adjustment chamber 18. Further, the NO while remaining in the form of NO passes through the second diffusion rate control member 32 and arrives at the oxygen concentration adjustment chamber 18.

The preliminary oxygen concentration control unit 106 applies the first voltage Va as the preliminary voltage Vp0 at the time of the first operation, and outputs the second voltage Vb as the preliminary voltage Vp0 at the time of the second operation. Moreover, in accordance with the oxygen concentration of the gas to be measured, the oxygen may be pumped into the preliminary chamber 21, and in such a case, the first voltage Va may be of a negative value. In cases where oxygen is neither pumped out nor pumped into the preliminary chamber 21, the first voltage Va may be set to Voff.

As described above, at the time of the first operation, the $NH_3$ component passes in the form of $NH_3$ through the second diffusion rate control member 32, and is reflected in the measurement pump current (sensor output) Ip3. Further, at the time of the second operation, the $NH_3$ component passes in the form of NO through the second diffusion rate control member 32, and is reflected in the measurement pump current (sensor output) Ip3. Since $NH_3$ is capable of being diffused through the second diffusion rate control member 32 more quickly than NO, the measurement pump current (sensor output) Ip3 undergoes a change between the time of the first operation and the time of the second operation. The magnitude of such a difference reflects the concentration of $NH_3$ within the gas to be measured. More specifically, the measurement pump current (sensor output) Ip3 can be decomposed into an NO component current and an $NH_3$ component current using the difference in the diffusion rates of $NH_3$ and NO. Accordingly, the gas sensor 10 determines the concentrations of NO and $NH_3$ on the basis of the difference between the sensor outputs from the specified component measurement unit 104, in accordance with the first and second operations of the preliminary oxygen concentration control unit 106.

Next, processing operations of the gas sensor 10 will be described with reference also to FIGS. 3 and 4.

Figure 3:
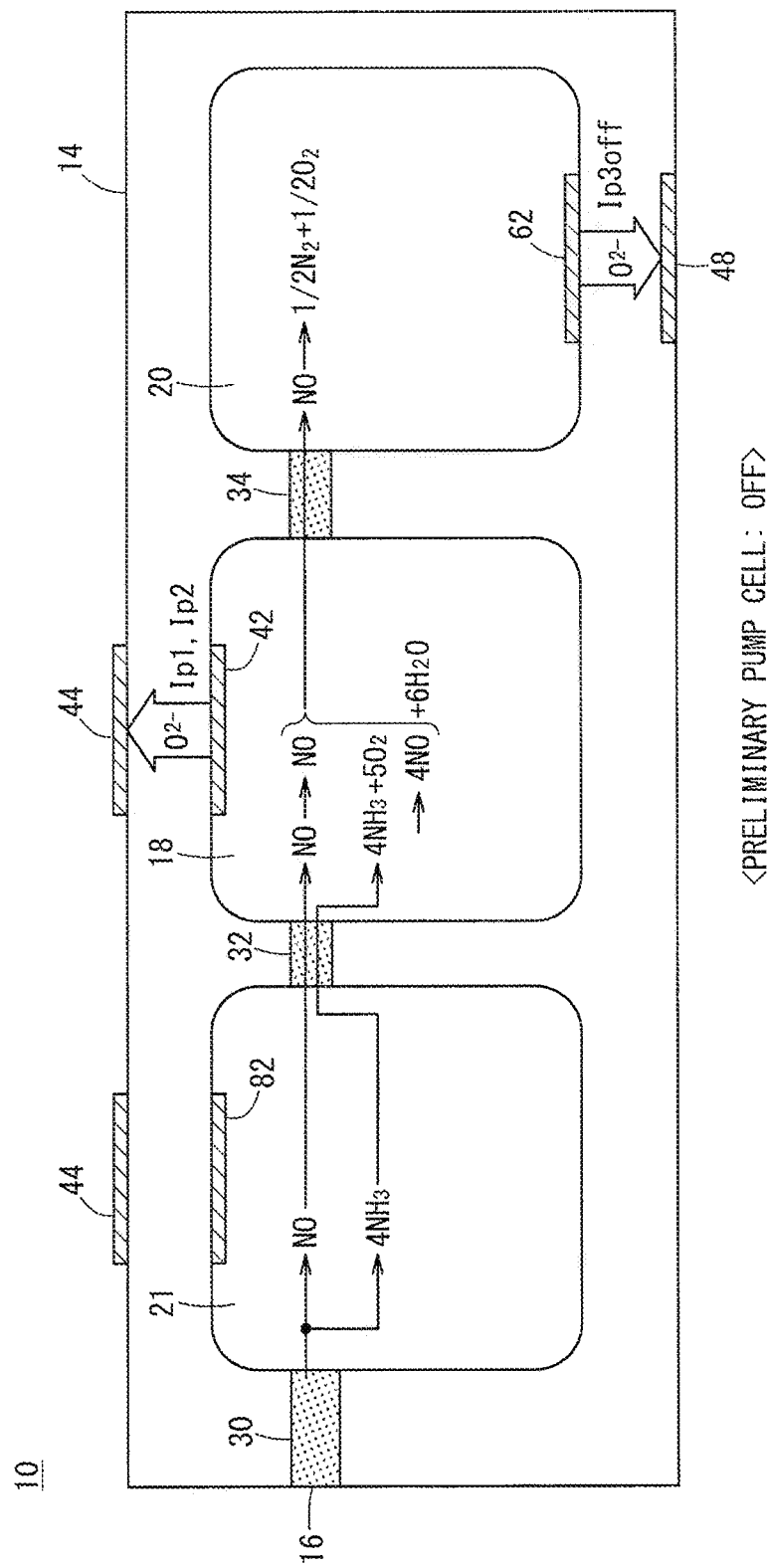
FIG. 3 is an explanatory diagram schematically showing reactions for a case in which a preliminary pump cell is turned OFF in the gas sensor of FIG. 1.

First, as shown in FIG. 3, the $NH_3$ that was introduced through the gas introduction port 16 reaches the oxygen concentration adjustment chamber 18 during a period in which the preliminary oxygen concentration control unit 106 is implementing the first operation by the drive control unit 108. In the oxygen concentration adjustment chamber 18, by operation of the oxygen concentration control unit 100, a control is performed so as to convert all of the $NH_3$ into NO, and therefore, the $NH_3$ that has flowed into the oxygen concentration adjustment chamber 18 from the preliminary chamber 21 causes a reaction in which oxidation from $NH_3$ into NO takes place inside the oxygen concentration adjustment chamber 18, and all of the $NH_3$ inside the oxygen concentration adjustment chamber 18 is converted into NO. Accordingly, the $NH_3$ that was introduced through the gas introduction port 16 passes through the first diffusion rate control member 30 and the second diffusion rate control member 32 at the $NH_3$ diffusion coefficient (for example, 2.2 $cm^2$/sec), and after being converted into NO inside the oxygen concentration adjustment chamber 18, passes through the third diffusion rate control member 34 at the NO diffusion coefficient (for example, 1.8 $cm^2$/sec), and moves into the adjacent measurement chamber 20.

Figure 4:
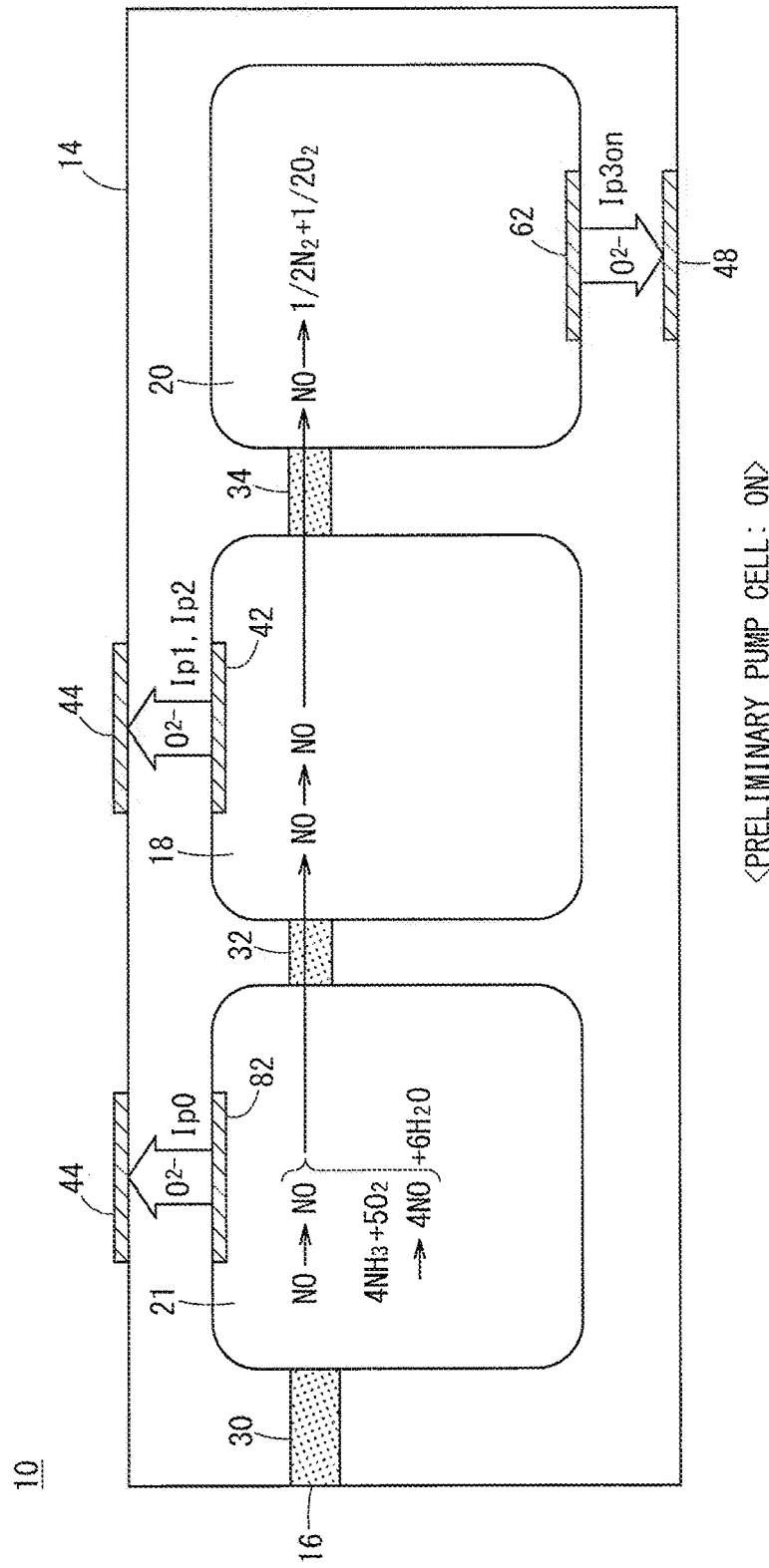
FIG. 4 is an explanatory diagram schematically showing reactions for a case in which a preliminary pump cell is turned ON in the gas sensor of FIG. 1.

On the other hand, during a period in which the preliminary oxygen concentration control unit 106 is implementing the second operation by the drive control unit 108, as shown in FIG. 4, the oxidation reaction from $NH_3$ into NO occurs inside the preliminary chamber 21, and all of the $NH_3$ that was introduced through the gas introduction port 16 is converted into NO. Accordingly, although the $NH_3$ passes through the first diffusion rate control member 30 at the $NH_3$ diffusion coefficient, after having passed through the second diffusion rate control member 32 on the innermost side from the preliminary chamber 21, movement into the measurement chamber 20 occurs at the NO diffusion coefficient.

Stated otherwise, by switching the preliminary oxygen concentration control unit 106 from the first operative state to the second operative state, the location where the oxidation reaction of $NH_3$ takes place is moved from the oxygen concentration adjustment chamber 18 to the preliminary chamber 21.

The movement of the location where the oxidation reaction of $NH_3$ takes place from the oxygen concentration adjustment chamber 18 to the preliminary chamber 21 equivalently implies that the state of the $NH_3$ within the gas to be measured when the $NH_3$ passes through the second diffusion rate control member 32 is changed from $NH_3$ into NO. In addition, since NO and $NH_3$ possess different diffusion coefficients, the difference between passing through the second diffusion rate control member 32 with NO or passing therethrough with $NH_3$ is manifested as a difference in the amount of NO that flows into the measurement chamber 20, and thus the measurement pump current Ip3 that flows to the measurement pump cell 61 is made to change.

In this case, the measurement pump current Ip3(Vb) when the second operation of the preliminary pump cell 80 is performed, and the amount of change ΔIp3 in the measurement pump current Ip3(Va) at the time of the first operation of the preliminary pump cell 80 are uniquely determined by the concentration of $NH_3$ within the gas to be measured. Therefore, it is possible to calculate the respective concentrations of NO and $NH_3$ from the measurement pump current Ip3(Vb) or Ip3(Va), and the amount of change ΔIp3 in the measurement pump current Ip3.

The target component acquisition unit 110 obtains the respective concentrations of NO and $NH_3$ on the basis of a first map 112 of the measurement pump current Ip3(Va) at the time of the first operation of the preliminary pump cell 80, and the amount of change ΔIp3 in the measurement pump currents Ip3 at the time of the first operation and at the time of the second operation. The first map 112 is a data group indicative of a correlation between the amount of change ΔIp3 and the $NH_3$ concentration, which is obtained in advance through experiment or simulation, and is made up from a plurality of sets of data groups corresponding to a plurality of different NO concentrations. Based on the measurement pump current Ip3off at a time that the preliminary pump cell 80 is turned OFF, the target component acquisition unit 110 determines which one of the correlations between the amount of change ΔIp3 and the $NH_3$ concentration corresponding to the NO concentration should be used, and on the basis of the corresponding amount of change ΔIp3, identifies the $NH_3$ concentration.

Further, the target component acquisition unit 110 may prospectively obtain a relationship between the amount of change ΔIp3 and the $NH_3$ concentration in advance through experiment or simulation, and may obtain the $NH_3$ concentration from the amount of change ΔIp3 at a time that the preliminary pump cell 80 is turned ON and at a time that the preliminary pump cell 80 is turned OFF. Then, the NO concentration may be obtained by subtracting the $NH_3$ concentration, which was obtained in the foregoing manner, from the NO concentration obtained from the sensor output at the time that the preliminary pump cell 80 was turned OFF, or in other words, the total NO concentration obtained by converting the total concentrations of NO and $NH_3$ into NO.

Next, with reference to the flowchart of FIG. 5 and the schematic diagram of FIG. 6, a description will be given concerning a process of acquiring the measurement pump current Ip3 (sensor output), and a process of acquiring the target component by the target component acquisition unit 110, which are implemented in the specified component measurement unit 104 of the gas sensor 10 as described above.

Figure 5:
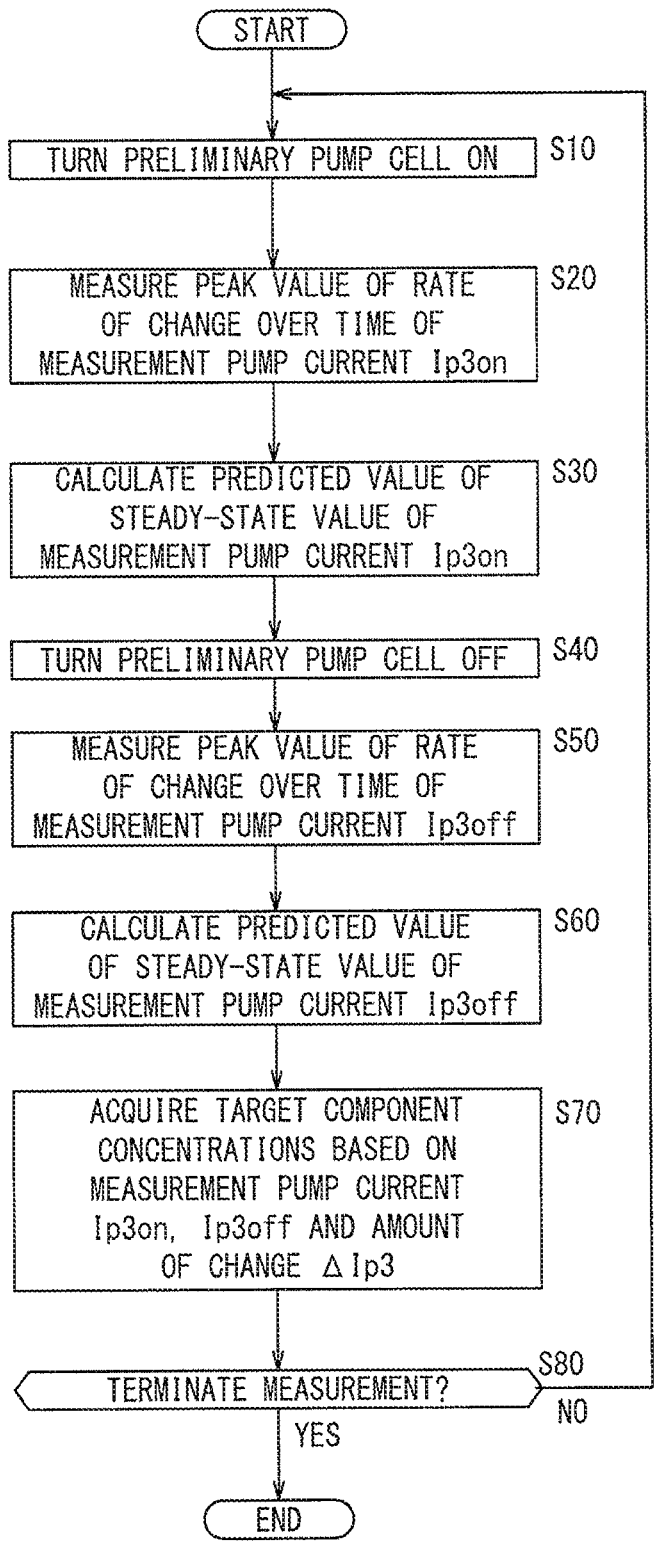
FIG. 5 is a flowchart showing a process of acquiring a measurement pump current Ip3 in the gas sensor of FIG. 1.

First, in step S10 of FIG. 5, the gas sensor 10 switches the preliminary pump cell 80 to ON (second operation). Consequently, the $NH_3$ within the gas to be measured is converted into NO inside the preliminary chamber 21, passes through the second diffusion rate control member 32, and based on a difference in the diffusion coefficients between NO and $NH_3$ in the second diffusion rate control member 32, the measurement pump current Ip3 flowing through the measurement pump cell 61 changes.

Figure 6:
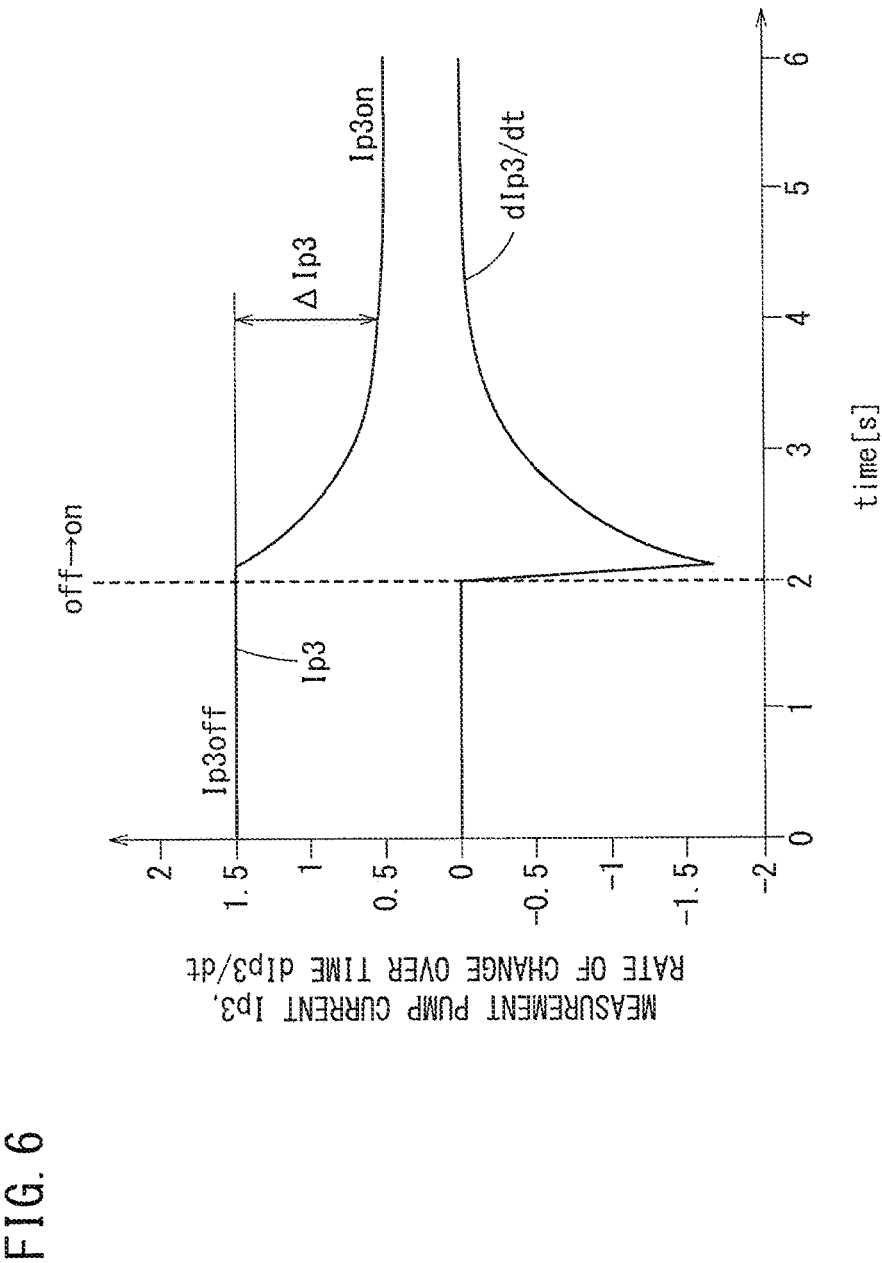

In this instance, when the operative state of the preliminary pump cell 80 is switched from OFF to ON, as shown in FIG. 6, the measurement pump current Ip3 settles to a steady-state value after a transitional change is performed, due to the diffusion resistance of the NO gas, an electrode reaction resistance on the surface of the measurement electrode, and delays of the respective pump voltage controls. The rate of change over time dIp3/dt of the measurement pump current Ip3 is large immediately after switching, and undergoes a change so as to settle to a constant value as time elapses. Further, the rate of change over time dIp3/dt of the measurement pump current Ip3 is roughly proportional to the amount of change amount ΔIp3, which is the difference between the measurement pump current Ip3on at a time that the preliminary pump cell 80 is turned ON, and the measurement pump current Ip3off at a time that the preliminary pump cell 80 is turned OFF. Thus, according to the present embodiment, attention is focused on the rate of change over time dIp3/dt of the measurement pump current Ip3.

More specifically, in step S20 of FIG. 5, the specified component measurement unit 104 acquires the peak value of the rate of change over time dIp3/dt of the measurement pump current Ip3on. As shown in FIG. 6, the peak value of the rate of change over time dIp3/dt of the measurement pump current Ip3on appears within 0.5 seconds from switching of the operative state of the preliminary pump cell 80, and the result is obtained more quickly than a time period on the order of 2 seconds until the measurement pump current Ip3on settles to a steady-state value.

Thereafter, in step S30 of FIG. 5, based on a transient peak value of the rate of change over time dIp3/dt of the measurement pump current Ip3on that was acquired in step S20, and a correlation that was determined beforehand through experiment or simulation, between the peak value of the rate of change over time dIp3/dt and the steady-state value of the measurement pump current Ip3on, the specified component measurement unit 104 obtains a predicted value of the steady-state value of the measurement pump current Ip3on.

Thereafter, in step S40, the gas sensor 10 switches the preliminary pump cell 80 to OFF (first operation). The time period during which the preliminary pump cell 80 continues in the ON state from step S10 until step S30, for example, a time period on the order of 0.5 seconds, can be made shorter than the time period (for example, on the order of 2 seconds) until the measurement pump current Ip3 settles to a steady-state value.

By the operative state of the preliminary pump cell 80 being switched from ON to OFF, the $NH_3$ within the gas to be measured inside the preliminary chamber 21 passes directly without change through the second diffusion rate control member 32, and as shown in FIG. 3, is converted into NO in the oxygen concentration adjustment chamber 18. Based on a difference in the diffusion coefficients between NO and $NH_3$ in the second diffusion rate control member 32, the measurement pump current Ip3 flowing through the measurement pump cell 61 changes.

At this time, when the operative state of the preliminary pump cell 80 is switched from ON to OFF, the measurement pump current Ip3 settles to a steady-state value after a transitional change is performed, due to the diffusion resistance of the NO gas, the electrode reaction resistance on the surface of the measurement electrode, and delays of the respective pump voltage controls. Further, the rate of change over time dIp3/dt of the measurement pump current Ip3 is roughly proportional to the amount of change amount ΔIp3, which is the difference between the measurement pump current Ip3off at the time that the preliminary pump cell 80 is turned OFF, and the measurement pump current Ip3on at the time that the preliminary pump cell 80 is turned ON. In step S50, the specified component measurement unit 104 measures a transient peak value of the rate of change over time dIp3/dt of the measurement pump current Ip3off.

Next, in step S60, based on the transient peak value of the rate of change over time dIp3/dt of the measurement pump current Ip3 that was acquired in step S50, and a correlation that was determined beforehand through experiment or simulation, between the peak value of the rate of change over time dIp3/dt and the steady-state value of the measurement pump current Ip3, the specified component measurement unit 104 obtains a predicted value of the steady-state value of the measurement pump current Ip3off.

In the following step S70, the target component acquisition unit 110 acquires the $NH_3$ concentration and the NO concentration, which are target components, based on the measurement pump current Ip3on obtained in step S30, the measurement pump current Ip3off obtained in step S60, and the amount of change ΔIp3 therebetween.

More specifically, based on the measurement pump current Ip3off at a time that the preliminary pump cell 80 is turned OFF, the target component acquisition unit 110 determines which one of the correlations of the first map 112 between the amount of change ΔIp3 and the $NH_3$ concentration corresponding to the NO concentration should be used, and on the basis of the corresponding amount of change ΔIp3, identifies the $NH_3$ concentration. Then, the target component acquisition unit 110 obtains the NO concentration by subtracting the $NH_3$ concentration, which was obtained in the foregoing manner, from the NO concentration obtained from the sensor output at the time that the preliminary pump cell 80 was turned OFF, or in other words, the total NO concentration obtained by converting the total concentrations of NO and $NH_3$ into NO.

Thereafter, in step S80, the gas sensor 10 checks whether or not an input to terminate measurement has been made. In the case that an input to terminate measurement has not been made, the process proceeds to step S10. In this case, the time period until switching from step S40 to step S10 may be shorter than the time period until the measurement pump current Ip3 becomes a steady-state value, and for example, can be on the order of 0.5 seconds.

On the other hand, in the case it is determined in step S80 that an input to terminate measurement has been made, the gas sensor 10 terminates the measurement process.

In the manner described above, according to the gas sensor 10 of the present embodiment, since the switching period between operations of the preliminary pump cell 80 can be shortened, it is possible to prevent a decrease in measurement accuracy due to a delay in the measurement time of the measurement pump current Ip3.

Experimental Example 1

A description will be given of an experimental example in which the gas sensor 10 of the present embodiment is used. In Experimental Example 1, six types of the gas to be measured, in which the NO concentration thereof was 0 ppm, and the $NH_3$ concentration thereof was 0 ppm, 100 ppm, 200 ppm, 300 ppm, 400 ppm, and 500 ppm, respectively, were supplied with respect to the gas sensor 10, and when the operative state of the preliminary pump cell 80 was switched from OFF to ON, the rate of change over time of the measurement pump current Ip3 was determined.

Figure 7:
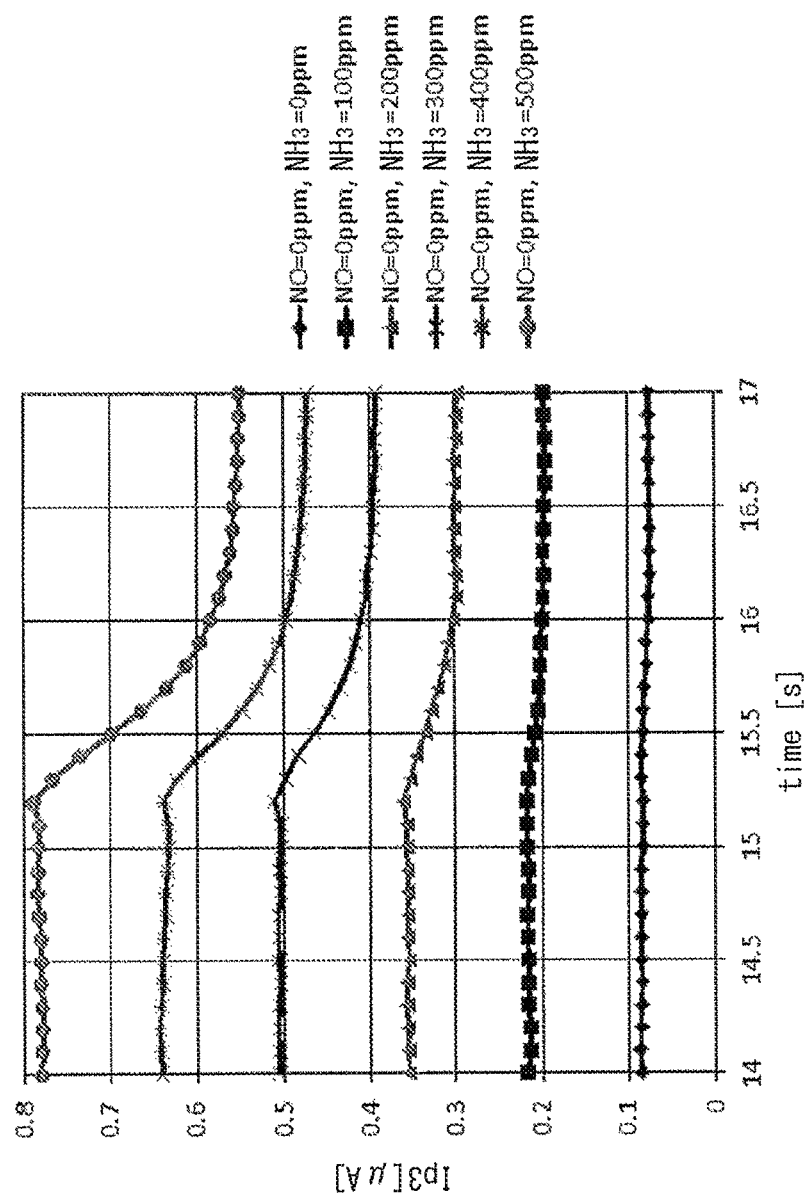
FIG. 7 is a graph showing measurement results of a change in the measurement pump current Ip3 accompanying switching of the operative state of the preliminary pump cell, under a condition in which the NO concentration of a gas to be measured is 0 ppm.

As shown in FIG. 7, in Experimental Example 1, the operative state of the preliminary pump cell 80 was switched at a time point of 15 seconds. It could be confirmed that the measurement pump current Ip3on converged to a steady-state value at a time period on the order of 2 seconds, regardless of the $NH_3$ concentration in the gas to be measured. Further, it could be confirmed that the slope of the measurement pump current Ip3 tends to increase as the $NH_3$ concentration increases.

Figure 8:
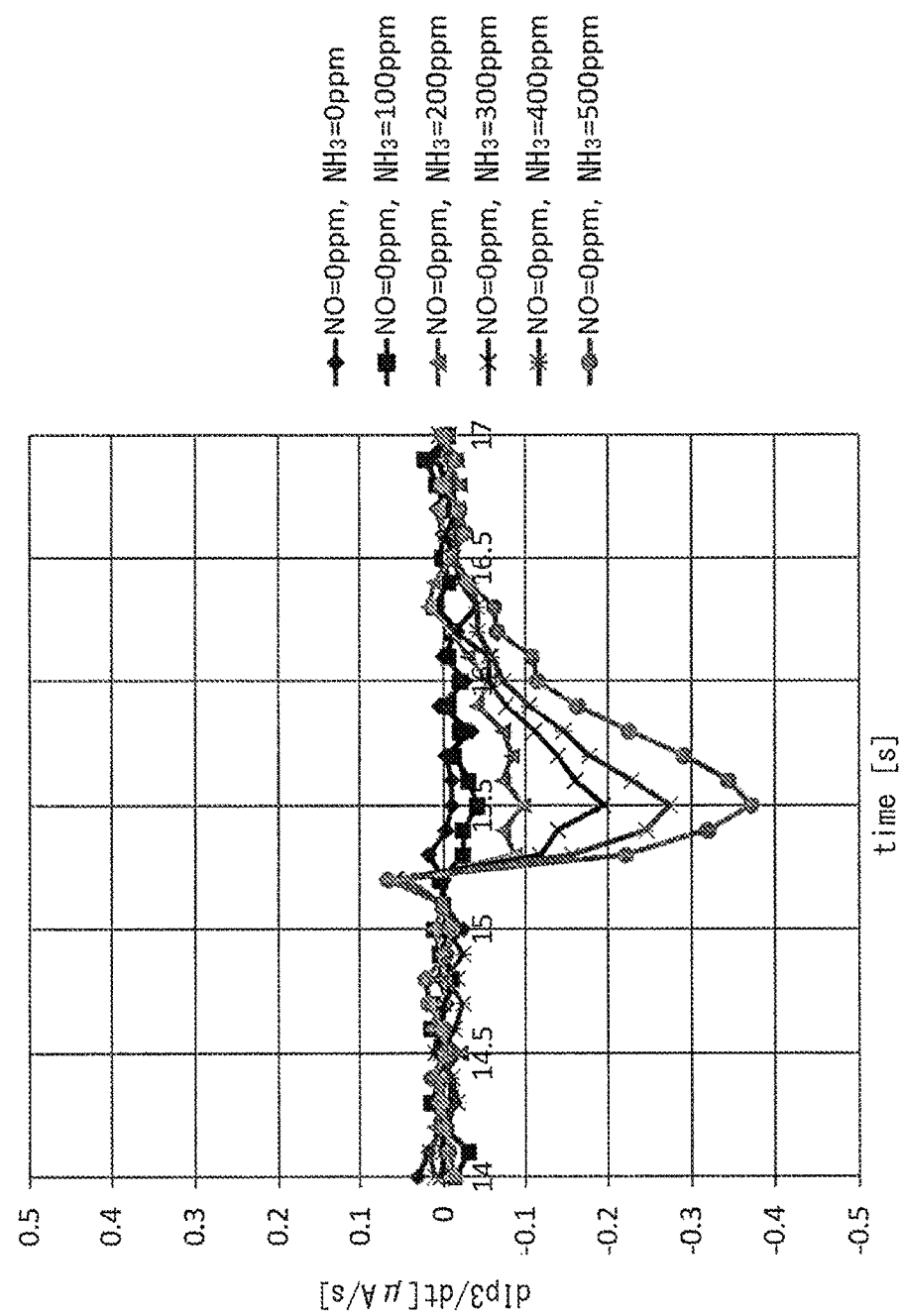
FIG. 8 is a graph showing the rate of change over time of the measurement pump current Ip3 shown in FIG. 7.

Upon obtaining the rate of change over time of the measurement pump current Ip3 for each of the gases to be measured, as shown in FIG. 8, it was shown that the peak values of the rate of change over time appear approximately 0.5 seconds after the switching time at 15 seconds of the preliminary pump cell 80, and the peak values have larger values as the change in the measurement pump current Ip3on after switching becomes greater. Further, it could be confirmed that a certain correlation exists between the rate of change over time of the measurement pump current Ip3 and the amount of change ΔIp3 of the measurement pump current Ip3 after switching. Accordingly, by acquiring the rate of change over time of the measurement pump current Ip3, it is possible to determine the steady-state value before the measurement pump current Ip3 converges to the steady-state value.

Figure 9:
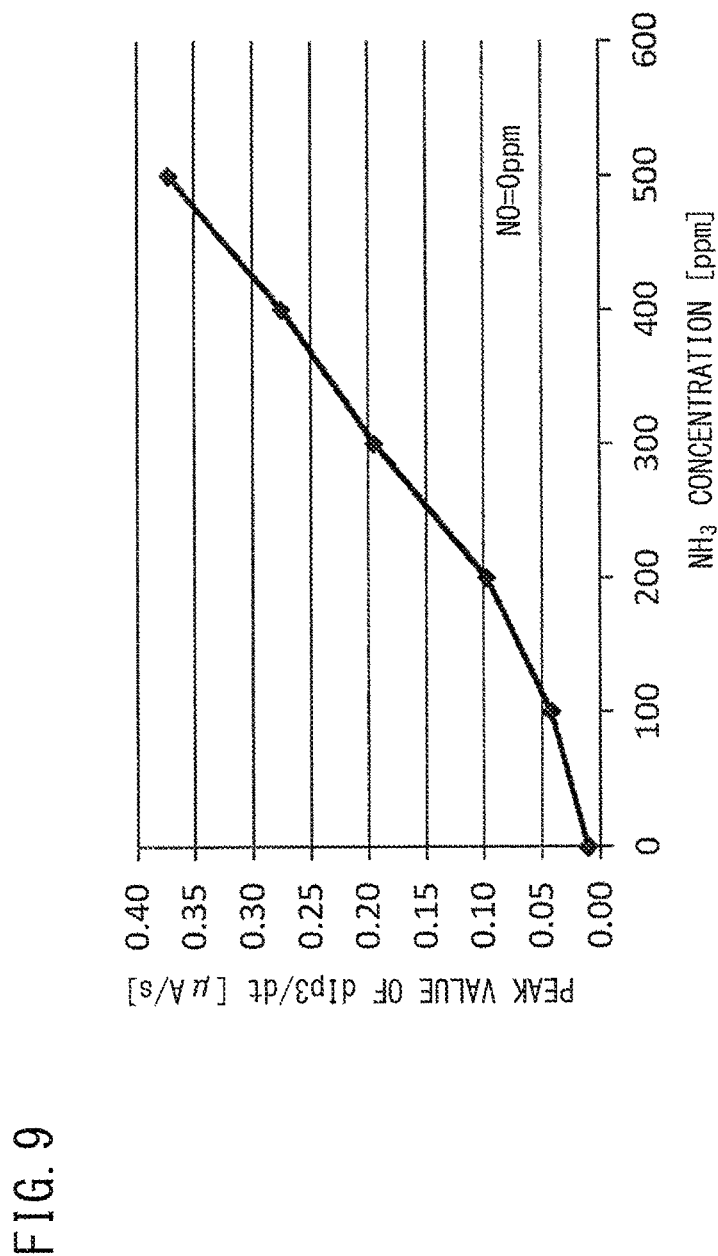
FIG. 9 is a graph showing a correlation between the $NH_3$ concentration and the rate of change over time of the measurement pump current Ip3 shown in FIG. 8.

As shown in FIG. 9, the rate of change over time dIp3/dt of the measurement pump current Ip3 changes substantially in proportion to the $NH_3$ concentration within the gas to be measured. Therefore, the $NH_3$ concentration within the gas to be measured can be determined directly from the rate of change over time dIp3/dt of the measurement pump current Ip3.

Experimental Example 2

Next, in Experimental Example 2, six types of the gas to be measured, in which the NO concentration thereof was 500 ppm, and the $NH_3$ concentration thereof was 0 ppm, 100 ppm, 200 ppm, 300 ppm, 400 ppm, and 500 ppm, respectively, were supplied with respect to the gas sensor 10, and when the operative state of the preliminary pump cell 80 was switched from OFF to ON, the rate of change over time of the measurement pump current Ip3 was determined.

Figure 10:
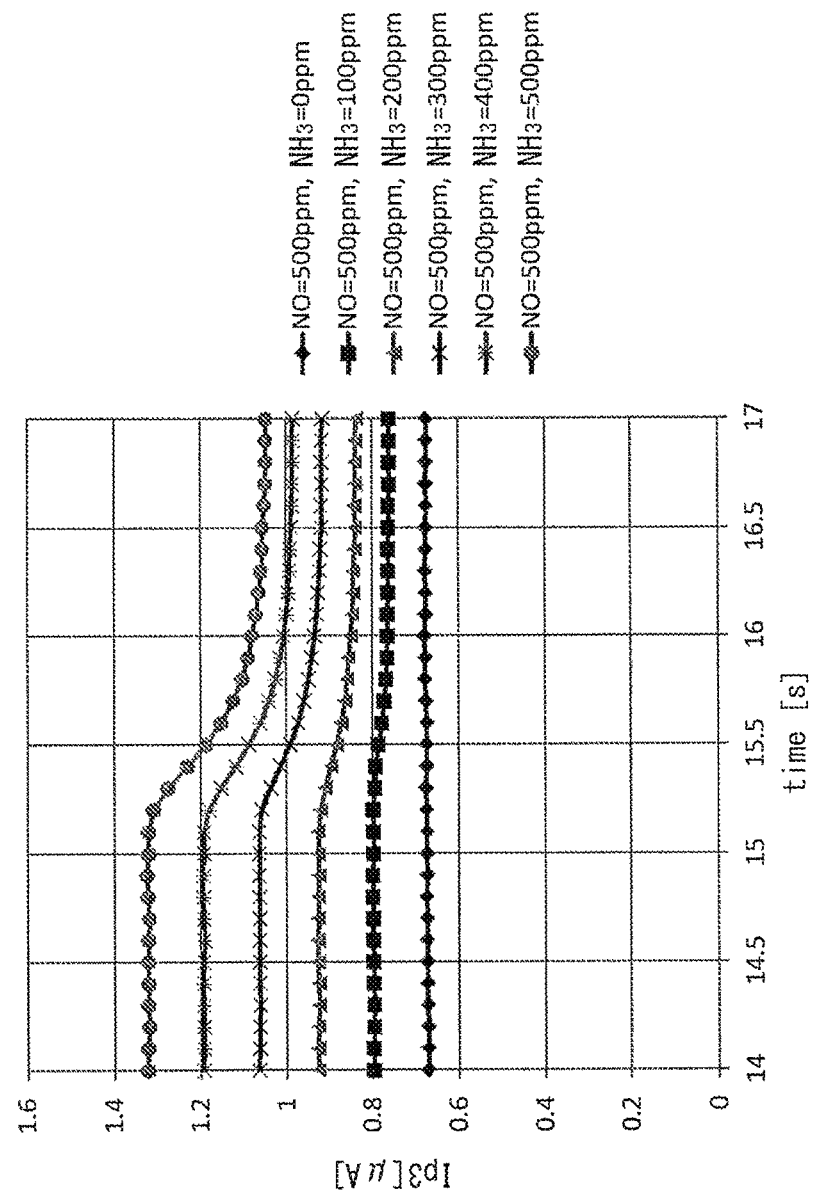
FIG. 10 is a graph showing measurement results of a change in the measurement pump current Ip3 accompanying switching of the operative state of the preliminary pump cell, under a condition in which the NO concentration of the gas to be measured is 500 ppm.
Figure 11:
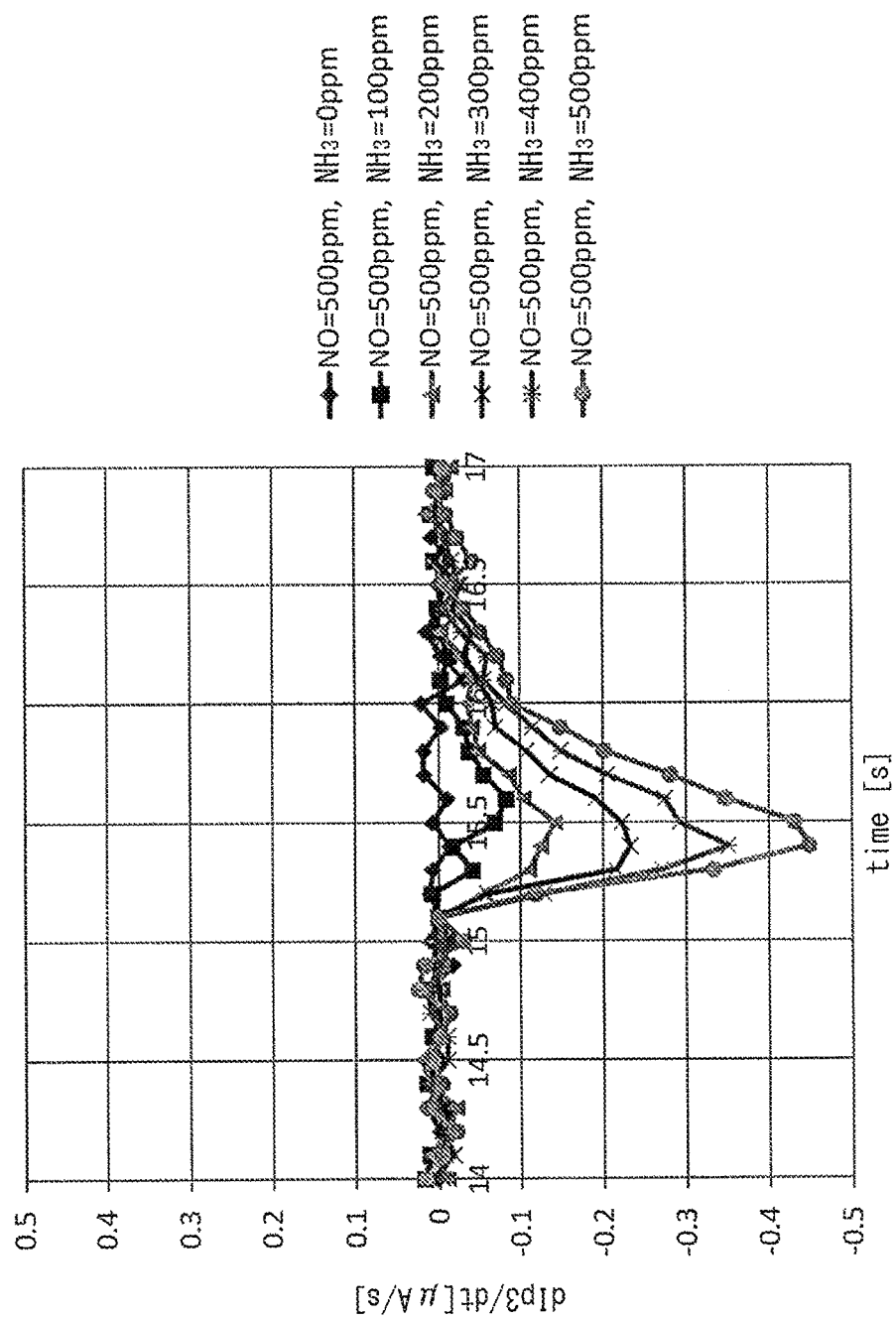
FIG. 11 is a graph showing the rate of change over time of the measurement pump current Ip3 shown in FIG. 10.

As shown in FIG. 10, even in the case that the NO concentration was 500 ppm, it could be confirmed that the slope of the measurement pump current Ip3 tends to increase as the $NH_3$ concentration increases. Further, as shown in FIG. 11, it could be confirmed that the peak values of the rate of change over time dIp3/dt of the measurement pump current Ip3 have larger values as the change in the measurement pump current Ip3on after switching becomes larger. Therefore, in accordance with Experimental Example 2, it could be confirmed that, even if the gas to be measured is mixed together with NO, the measurement pump current Ip3on (steady-state value) can be determined from the peak value of the rate of change over time dIp3/dt of the measurement pump current Ip3. Further, the peak value of the rate of change over time dIp3/dt of the measurement pump current Ip3 can be determined at a time period on the order of 0.5 seconds, and it is possible to determine the measurement pump current Ip3on without having to wait until the measurement pump current Ip3 converges to a steady-state value.

Figure 12:
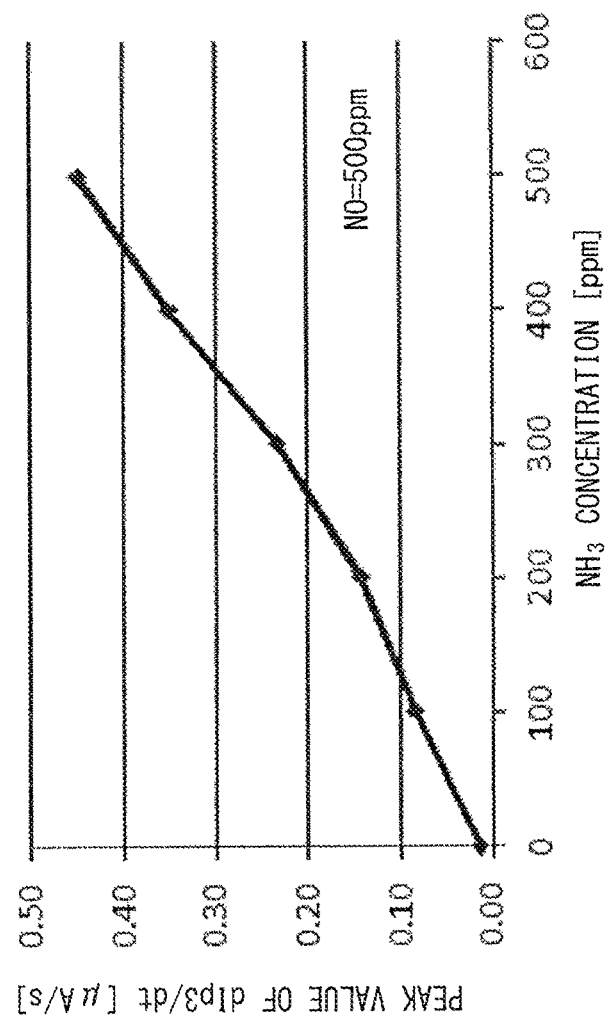
FIG. 12 is a graph showing a correlation between the NH3 concentration and a peak value of the rate of change over time shown in FIG. 11.

Furthermore, as shown in FIG. 12, it could be confirmed that, even if the gas to be measured is mixed together with NO, a correlation exists between the peak value of the rate of change over time dIp3/dt of the measurement pump current Ip3 and the $NH_3$ concentration within the gas to be measured. Therefore, on the basis of the correlation shown in FIG. 12, the $NH_3$ together with 500 ppm of NO can be directly obtained from the rate of change over time dIp3/dt of the measurement pump current Ip3.

Experimental Example 3 and Comparative Example

In order to confirm the advantages realized by the gas sensor 10 and the concentration measurement method of the present embodiment, differences in measurement results for a case in which the switching period of the operative state of the preliminary pump cell 80 was set to 4 seconds (0.25 Hz) (Comparative Example), and a case in which the switching period was set to 1 second (1 Hz) (Experimental Example 3) were confirmed by way of a simulation calculation. Regarding the NO concentration and the $NH_3$ concentration of the gas to be measured, results thereof, which were measured by an FT-IR method, are shown by the solid lines in FIGS. 13 and 14.

In this instance, the measurement pump current Ip3on and the measurement pump current Ip3off were determined approximately by multiplying each of the NO concentration and the $NH_3$ concentration obtained by the FT-IR method, by a unique coefficient and adding them together. More specifically, the measurement pump current Ip3off was determined by multiplying the NO concentration (t1) and the $NH_3$ concentration (t1) obtained by the FT-IR method at a desired measurement time t1, respectively, by predetermined coefficients and adding them together. Further, the measurement pump current Ip3on was determined by multiplying the NO concentration (t2) and the $NH_3$ concentration (t2) obtained by the FT-IR method at time t2 one half-period before the time t1, respectively, by predetermined coefficients and adding them together. Moreover, in this instance, in order that attention is paid to variations in the measurement pump current Ip3on and the measurement pump current Ip3off, the values of the coefficients themselves that are multiplied by the NO concentration and the $NH_3$ concentration may be appropriately selected. The NO concentration and the $NH_3$ concentration, which were determined on the basis of the first map 112, are plotted in FIGS. 13 and 14 with respect to the measurement pump current Ip3off and the measurement pump current Ip3on, which were obtained by the above-described method.

Figure 13:
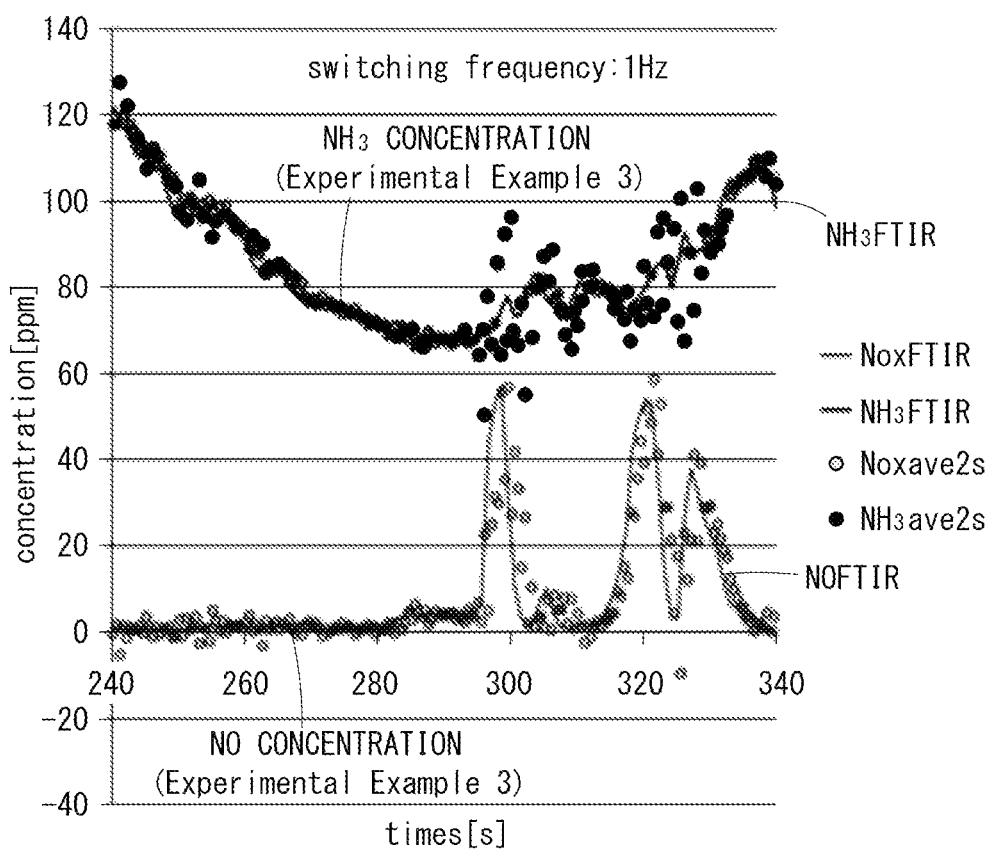
FIG. 13 is a graph showing measurement results of a change in the $NH_3$ concentration in a gas to be measured according to an FT-IR method, and results (Experimental Example 3) of having determined by simulation a detection value of the $NH_3$ concentration by the gas sensor shown in FIG. 1, for a case in which an operation switching period of the preliminary pump cell was set to 1 second (1 Hz)

For the case in which the switching period is 1 second (1 Hz), as in Experimental Example 3 of FIG. 13, it can be understood that the delay in the measurement time of the NO concentration and the $NH_3$ concentration is limited to 0.5 seconds, and any decrease in the measurement accuracy is suppressed.

Figure 14:
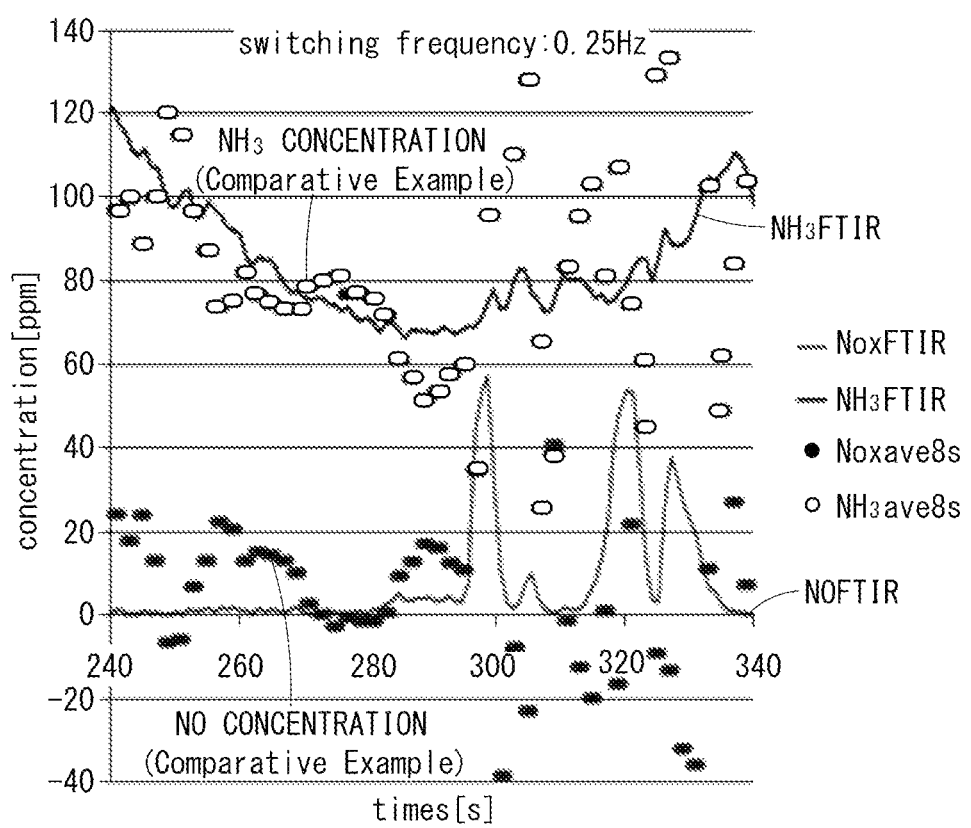
FIG. 14 is a graph showing measurement results of a change in the $NH_3$ concentration in a gas to be measured according to an FT-IR method, and results (Comparative Example) of having determined by simulation a detection value of the $NH_3$ concentration by the gas sensor shown in FIG. 1, for a case in which the operation switching period of the preliminary pump cell was set to 4 seconds (0.25 Hz)

On the other hand, for the case in which the switching period is 4 seconds (0.25 Hz), as in the comparative example of FIG. 14, it can be understood that the delay in the measurement time of the NO concentration and the $NH_3$ concentration is on the order of 2 seconds, and in relation to the measurement results obtained by the FT-IR method, significant errors occur.

The gas sensor 10 and the gas concentration measurement method according to the present embodiment as described above exhibit the following advantages.

In the gas sensor 10 and the gas concentration measurement method of the present embodiment, the preliminary oxygen concentration control unit 106 (preliminary pump cell 80) carries out switching operations between the first operation (OFF) and the second operation (ON) within a period that is shorter than a standby time until the measurement pump current Ip3 converges to a steady-state value. Consequently, since the measurement period is made shorter, a decrease in measurement accuracy due to a delay in the measurement time can be suppressed.

Second Embodiment

A description will be given concerning another example of a process of acquiring the measurement pump current Ip3 (sensor output) implemented by the specified component measurement unit 104, and a process of acquiring the target component by the target component acquisition unit 110, of the gas sensor 10.

As shown in FIGS. 9 and 12, the peak value of the rate of change over time dIp3/dt of the measurement pump current Ip3 has a correlation with the $NH_3$ concentration within the gas to be measured. Thus, according to the present embodiment, the specified component measurement unit 104 determines the $NH_3$ concentration directly from the correlation between the peak value of the rate of change over time dIp3/dt of the measurement pump current Ip3 and the $NH_3$ concentration in the gas to be measured.

As shown in the flowchart of FIG. 15, in step S110, the gas sensor 10 switches the operative state of the preliminary pump cell 80 to ON. Thereafter, in step S120, the specified component measurement unit 104 obtains the peak value of the rate of change over time dIp3/dt of the measurement pump current Ip3on.

Thereafter, in step S130, with reference to the second map 114, from the peak value of the rate of change over time dIp3/dt of the measurement pump current Ip3, the specified component measurement unit 104 determines the $NH_3$ concentration within the gas to be measured.

Next, in step S140, the gas sensor 10 switches the operative state of the preliminary pump cell 80 to OFF. Thereafter, in step S150, the specified component measurement unit 104 acquires the peak value of the rate of change over time dIp3/dt of the measurement pump current Ip3off.

Next, in step S160, the specified component measurement unit 104 determines the steady-state value of the measurement pump current Ip3off (predicted value), from the peak value of the rate of change over time dIp3/dt of the measurement pump current Ip3 that was acquired in step S150.

Thereafter, in step S170, the target component acquisition unit 110 determines the total NO concentration from the measurement pump current Ip3off (predicted value), and then subtracts the $NH_3$ concentration obtained in step S130 from the total NO concentration, thereby acquiring the concentration of NO, which is the target component, within the gas to be measured.

Next, in step S180, the gas sensor 10 detects whether or not an input to terminate measurement has been made, and in the case that an input to terminate measurement has not been made, the process returns to step S110 and measurement is continued, whereas in the case that an input to terminate measurement has been made, the measurement process is terminated.

In the foregoing manner, in the gas sensor 10 and the gas concentration measurement method of the present embodiment, the specified component measurement unit 104 may use the second map 114 which registers a relationship between the concentration of the specified component within the gas to be measured, which is measured experimentally beforehand, and a point specified by the peak values of the rate of change over time dIp3/dt of the measurement pump current Ip3, which is measured experimentally beforehand, accompanying switching operations between the time of the first operation and the time of the second operation of the preliminary oxygen concentration control unit 106 (preliminary pump cell 80), and may acquire the concentration of the specified component ($NH_3$) within the gas to be measured, by comparing with the second map 114 the peak values of the rate of change over time dIp3/dt of the measurement pump current Ip3 from the specified component measurement unit 104, upon switching operations of the preliminary oxygen concentration control unit 106 (preliminary pump cell 80) during actual use thereof.

Although the present invention has been described above by way of preferred embodiments, the present invention is not limited to the above-described embodiments, and it goes without saying that various modifications can be made within a range that does not depart from the essence and gist of the present invention.

What is claimed is:

1. A gas sensor configured to measure concentrations of a plurality of components existing in presence of oxygen, comprising:
   a structural body made up from a solid electrolyte that exhibits oxygen ion conductivity;
   a gas introduction port formed in the structural body and into which a gas to be measured is introduced;
   a preliminary chamber including a preliminary pump electrode and communicating with the gas introduction port;
   an oxygen concentration adjustment chamber including a pump electrode and communicating with the preliminary chamber;
   a measurement chamber including a measurement electrode and communicating with the oxygen concentration adjustment chamber;
   a preliminary oxygen concentration control unit configured to control an oxygen concentration inside the preliminary chamber based on a voltage of the preliminary pump electrode;
   a specified component measurement unit configured to detect a measurement pump current (Ip3) flowing through an exterior side pump electrode and the measurement electrode, under an operation of the preliminary oxygen concentration control unit; and
   a target component acquisition unit configured to acquire a concentration of a target component within the gas to be measured, on a basis of an amount of change ($\Delta Ip3$) between a measurement pump current (Ip3on) from the specified component measurement unit at a time of a first operation of the preliminary oxygen concentration control unit and a measurement pump current (Ip3off) from the specified component measurement unit at a time of a second operation of the preliminary oxygen concentration control unit, and one of the measurement pump current (Ip3on) and the measurement pump current (Ip3off);

wherein the specified component measurement unit is configured to determine a steady-state value of the measurement pump current (Ip3on) or a steady-state value of the measurement pump current (Ip3off), based on a peak value of a rate of change over time of the measurement pump current (Ip3) when an operation of the preliminary oxygen concentration control unit is switched between the first operation and the second operation.

2. The gas sensor according to claim 1, wherein the preliminary oxygen concentration control unit carries out switching operations between the first operation and the second operation within a period that is shorter than a standby time until the measurement pump current converges to the steady-state value.

3. The gas sensor according to claim 1, wherein the specified component measurement unit is configured to:
use a map which registers a relationship between a concentration of a specified component within the gas to be measured, which is measured experimentally beforehand, and a point specified by the peak value of the rate of change over time of the measurement pump current (Ip3), which is measured experimentally beforehand, accompanying the switching operation between the first operation and the second operation of the preliminary oxygen concentration control unit; and
acquire the concentration of the specified component within the gas to be measured, by comparing with the map a peak value of a rate of change over time of the measurement pump current (Ip3) from the specified component measurement unit, upon a switching operation of the preliminary oxygen concentration control unit during actual use thereof.

4. The gas sensor according to claim 3, wherein the specified component is $NH_3$.

5. The gas sensor according to claim 1, wherein the oxygen concentration adjustment chamber includes a main chamber and an auxiliary chamber, the main chamber communicating with the preliminary chamber, and the auxiliary chamber communicating with the measurement chamber.

6. A gas concentration measurement method in which a gas sensor is used, the gas sensor comprising a structural body made up from a solid electrolyte that exhibits oxygen ion conductivity, a gas introduction port formed in the structural body and into which a gas to be measured is introduced, a preliminary chamber including a preliminary pump electrode and communicating with the gas introduction port, an oxygen concentration adjustment chamber including a pump electrode and communicating with the preliminary chamber, a measurement chamber including a measurement electrode and communicating with the oxygen concentration adjustment chamber, a preliminary oxygen concentration control unit configured to control an oxygen concentration inside the preliminary chamber based on a voltage of the preliminary pump electrode, a specified component measurement unit configured to detect a measurement pump current (Ip3) flowing through an exterior side pump electrode and the measurement electrode under an operation of the preliminary oxygen concentration control unit, and a target component acquisition unit configured to acquire a concentration of a target component within the gas to be measured, on a basis of an amount of change ($\Delta$Ip3) between a measurement pump current (Ip3on) from the specified component measurement unit at a time of a first operation of the preliminary oxygen concentration control unit and a measurement pump current (Ip3off) from the specified component measurement unit at a time of a second operation of the preliminary oxygen concentration control unit, and one of the measurement pump current (Ip3on) and the measurement pump current (Ip3off), the gas concentration measurement method comprising:

an operation switching step of performing a control to switch between the first operation and the second operation of the preliminary oxygen concentration control unit;

a determining step of, by the specified component measurement unit, determining a peak value of a rate of change over time of the measurement pump current (Ip3) accompanying the control to switch between the first operation and the second operation of the preliminary oxygen concentration control unit;

a determining step of, by the specified component measurement unit, determining a steady-state value of the measurement pump current (Ip3), from a previously determined correlation between the peak value of the rate of change over time of the measurement pump current (Ip3) and the steady-state value of the measurement pump current (Ip3); and an acquisition step of, by the target component acquisition unit, acquiring the concentration of the target component within the gas to be measured, based on the steady-state value of the measurement pump current (Ip3) from the specified component measurement unit.

7. The gas concentration measurement method according to claim 6, wherein the control to switch between the first operation and the second operation of the preliminary oxygen concentration control unit is carried out repeatedly at a period that is shorter than a time until the measurement pump current (Ip3) converges to the steady-state value.

8. The gas concentration measurement method according to claim 6, wherein the gas component measurement method comprises a specified component acquisition step, in which the specified component measurement unit uses a map which registers a relationship between a concentration of a specified component within the gas to be measured, which is measured experimentally beforehand, and a point specified by the peak value of the rate of change over time of the measurement pump current (Ip3), which is measured experimentally beforehand, accompanying a switching operation between the first operation and the second operation of the preliminary oxygen concentration control unit, and the specified component measurement unit acquires the concentration of the specified component within the gas to be measured, by comparing with the map a peak value of a rate of change over time of the measurement pump current (Ip3) from the specified component measurement unit, upon a switching operation of the preliminary oxygen concentration control unit during actual use thereof.

9. The gas concentration measurement method according to claim 8, wherein the specified component is $NH_3$.

10. The gas concentration measurement method according to claim 6, wherein the oxygen concentration adjustment chamber includes a main chamber and an auxiliary chamber, the main chamber communicating with the preliminary chamber, and the auxiliary chamber communicating with the measurement chamber.

* * * * *